(12) United States Patent
Atkinson et al.

(10) Patent No.: US 8,383,635 B2
(45) Date of Patent: Feb. 26, 2013

(54) CHEMICAL COMPOUNDS

(75) Inventors: Francis Louis Atkinson, Harlow (GB); Jeffrey Michael Axten, Collegeville, PA (US); Maria Cichy-Knight, Collegeville, PA (US); Michael Lee Moore, Collegeville, PA (US); Vipulkumar Kantibhai Patel, Stevenage (GB); Xinrong Tian, Collegeville, PA (US); Christopher Roland Wellaway, Stevenage (GB); Allison K. Dunn, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 50 days.

(21) Appl. No.: 13/058,251

(22) PCT Filed: Aug. 12, 2009

(86) PCT No.: PCT/US2009/053504
§ 371 (c)(1), (2), (4) Date: Feb. 9, 2011

(87) PCT Pub. No.: WO2010/019637
PCT Pub. Date: Feb. 18, 2010

(65) Prior Publication Data
US 2011/0136838 A1 Jun. 9, 2011

Related U.S. Application Data

(60) Provisional application No. 61/088,113, filed on Aug. 12, 2008.

(51) Int. Cl.
*A01N 43/90* (2006.01)
*A61K 31/519* (2006.01)
*C07D 471/00* (2006.01)

(52) U.S. Cl. ................................. 514/264.11; 544/279
(58) Field of Classification Search ....................... None
See application file for complete search history.

(56) References Cited

U.S. PATENT DOCUMENTS
6,174,889 B1   1/2001   Cockerill et al.
6,420,375 B1   7/2002   Aono et al.

FOREIGN PATENT DOCUMENTS
WO   WO 2008/079988 A2   7/2008

*Primary Examiner* — Jeffrey Murray
(74) *Attorney, Agent, or Firm* — Adrea V. Lockenour; Edward R. Gimmi

(57) ABSTRACT

The invention is directed to pyrido[4,3-d]pyrimidin-5(6H)-one derivatives. Specifically, the invention is directed to compounds according to Formula I:

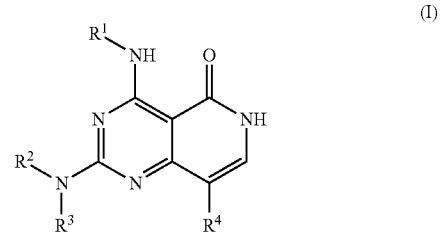

wherein $R^1$, $R^2$, $R^3$, and $R^4$ are defined below.

The compounds of the invention are inhibitors of PDK1 and can be useful in the treatment of disorders characterized by constitutively activated ACG kinases such as cancer and more specifically cancers of the breast, colon, and lung. Accordingly, the invention is further directed to pharmaceutical compositions comprising a compound of the invention. The invention is still further directed to methods of inhibiting PDK1 activity and treatment of disorders associated therewith using a compound of the invention or a pharmaceutical composition comprising a compound of the invention.

9 Claims, No Drawings

CHEMICAL COMPOUNDS

CROSS REFERENCE TO PRIOR APPLICATION

This application is the US National Stage of International Application No. PCT/US2009/053504, filed 12 Aug. 2009, which is incorporated herein by reference. This application also claims benefit of the filing date of U.S. 61/088,113 filed 12 Aug. 2008.

FIELD OF THE INVENTION

The present invention relates to pyrido[4,3-d]pyrimidin-5 (6H)-one derivatives that are inhibitors of the activity of the serine/threonine kinase, PDK1. The present invention also relates to pharmaceutical compositions comprising such compounds and methods of using such compounds in the treatment of cancer.

BACKGROUND OF THE INVENTION

Activation of the phosphoinositide-3 kinase (PI-3K) pathway constitutes one of the most important mechanisms that regulates important cellular functions such as gene expression, cell cycle progression, cell growth, and differentiation (Dygas and Baranska, *Acta Biochim. Pol.* 48:541-549 (2001)). Modification of AKT and other PI-3K downstream kinases in the cytosol is mediated by 3-phosphoinositide dependent kinase 1 (PDK1), a serine/threonine kinase originally identified as a kinase critical for AKT activation loop phosphorylation and activation (Cohen et al., *FEBS Lett.*, 410:3-10 (1997)).

Substrates of PDK1 include many of the AGC family of protein kinases (the cAMP-dependent, cGMP-dependent, and protein kinase C), including AKT/PKB, p70S6K, cyclic AMP-dependent protein kinase, protein kinase C, serum and glucocorticoid-inducible kinase (SGK), p90 ribosomal protein kinase (RSK), p21-activated kinase-1 (PAK1) PRK1/2, and others (Wick and Liu, *Curr. Drug Targets Immune Endocr. Metabol. Disord.* 1:209-221 (2001); Mora et al., *Semin. Cell Dev. Biol.* 15:161-170 (2004)). However, recent in vivo studies with PDK1(−/−) and PDK1(−/+) mice showed that the most physiologically relevant substrates of PDK1 are AKT, p70S6K and RSK (Lawlor et al *EMBO J.* 21:3728-3738 (2002); Williams et al., *Curr. Biol.* 10:439-448 (2000)). Activation of these critical PDK1 substrates leads to an increase in glucose uptake, protein synthesis, and inhibition of pro-apoptotic proteins.

Regulation of AKT is a best studied example of the PI3K-dependent activity of PDK1. Specific inhibitors of PI3K or dominant negative AKT mutants abolish survival-promoting activities of growth factors or cytokines. It has been previously described that inhibitors of PI3K (LY294002 or wortmannin) blocked the activation of AKT by upstream kinases. In addition, introduction of constitutively active PI3K or AKT mutants promotes cell survival under conditions in which cells normally undergo apoptotic cell death (Kulik et al., *Mol. Cell Biol.* 17(3):1595-1606 (1997); Dudek et al, *Science* 275 (5300):661-665 (1997)).

Analysis of AKT levels in human tumors revealed that AKT is overexpressed in a significant number of ovarian (Cheung et al., *Proc. Natl. Acad. Sci. U.S.A.* 89:9267-9271 (1992)) and pancreatic cancers (Cheung et al., *Proc. Natl. Acad. Sci. U.S.A.* 93:3636-3641 (1996)). Also, AKT was found to be overexpressed in breast and prostate cancer cell lines (Nakatani et al. *J. Biol. Chem.* 274:21528-21532 (1999)).

A significant number of cancers possess mutations in genes that result in elevation of cellular levels of phosphatidylinositol 3,4,5-triphosphate (PIP3), a product of PI3K. One of the most common mutations giving rise to higher levels of PIP3 is in the PIP3 3-phosphatase PTEN gene (Leslie and Downes, *Cell Signal.* 14:285-295 (2002); Cantley, *Science* 296:1655-1657 (2002)). Increased levels of PIP3 result in over-activation of AKT and p70S6K kinases, which are thought to function as major driving forces in promoting the uncontrolled proliferation and enhanced survival of these cells. Germline mutations of PTEN are responsible for human cancer syndromes such as Cowden disease (Liaw et al., *Nature Genetics* 16:64-67 (1997)). PTEN is deleted in a large percentage of human tumors and tumor cell lines without functional PTEN show elevated levels of activated AKT (Li et al. supra, Guldberg et al., *Cancer Research* 57:3660-3663 (1997), Risinger et al., *Cancer Research* 57:4736-4738 (1997)).

Three members of the AKT/PKB subfamily of second-messenger regulated serine/threonine protein kinases have been identified and termed AKT1, AKT2 and AKT3. The isoforms are homologous, particularly in regions encoding the catalytic domains. AKTs are activated by phosphorylation events occurring in response to PI3K signaling. PI3K phosphorylates membrane inositol phospholipids, generating the second messengers phosphatidylinositol 3,4,5-triphosphate (PIP3) and phosphatidylinositol 3,4-diphosphate, which have been shown to bind to the PH domain of AKT. The current model of AKT activation proposes recruitment of the enzyme to the membrane by PIP3. PDK1 also possesses the PH domain and it is postulated that co-localization of AKT and PDK1 at the membrane allows for AKT modification and activation by PDK1 and possibly other kinases (Hemmings, *Science* 275:628-630 (1997); Hemmings, *Science* 276:534 (1997); Downward, *Science* 279:673-674 (1998)).

Phosphorylation of AKT1 occurs on two regulatory sites, Thr308 by PDK1 in the catalytic domain activation loop and Ser473 (most probably by TORC2 mTOR complex) near the carboxy terminus (Alessi et al., *EMBO J.* 15:6541-6551 (1996); Meier et al., *J. Biol. Chem.* 272:30491-30497 (1997)).

Important non-PI3K-dependent physiological substrates of PDK1, p90 ribosomal protein S6 kinases (RSKs) have been recently implicated in promoting tyrosine receptor-induced hematopoetic transformation (Kang et al., *Cancer Cell* 12:201-214 (2007)). PDK1 activates RSK by phosphorylating its amino terminal kinase domain in an ERK-dependent manner (Cohen et al., *Nature Chem. Biol.* 3(3):156-160 (2007)).

Also, recent studies revealed additional roles of PDK1 that could be important during tumorigenesis and metastasis, such as cell motility and migration (Primo et al., *J. Cell Biol.* 176(7):1035-1047 (2007); Pinner and Sahai, *Nature Cell Biol.* 10(2):127-137 (2008)).

Taken together, these observations suggest that an inhibitor of PDK1 might be beneficial for treatment of cancer cells possessing (but not limited to) constitutively activated AGC kinases.

SUMMARY OF THE INVENTION

The invention is directed to pyrido[4,3-d]pyrimidin-5 (6H)-one derivatives. Specifically, the invention is directed to compounds according to Formula I:

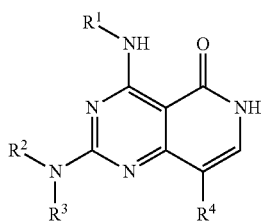

wherein R¹, R², R³, and R⁴ are defined below.

The compounds of the invention are inhibitors of PDK1 and can be useful in the treatment of disorders characterized by constitutively activated ACG kinases such as cancer and more specifically cancers of the breast, colon, and lung. Accordingly, the invention is further directed to pharmaceutical compositions comprising a compound of the invention. The invention is still further directed to methods of inhibiting PDK1 activity and treatment of disorders associated therewith using a compound of the invention or a pharmaceutical composition comprising a compound of the invention.

DETAILED DESCRIPTION OF THE INVENTION

The invention is directed to compounds according to Formula I:

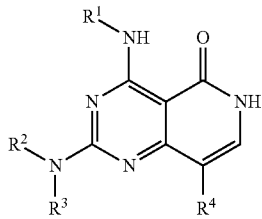

wherein:
$R^1$ is aryl, —$CH_2$-aryl, or heteroaryl each of which is optionally substituted with one to three $R^5$;
$R^2$ is H, $C_1$-$C_6$ alkyl optionally substituted with one or two $R^6$, $C_3$-$C_6$ cycloalkyl optionally substituted with one to three $R^7$, or heterocycloalkyl optionally substituted with one to three $R^7$; and $R^3$ is H, $C_1$-$C_6$ alkyl, or phenyl;
or
$R^2$ and $R^3$ are joined together with the nitrogen atom to which they are attached forming a saturated 4-7 membered heterocycloalkyl which may contain one additional N, S, or O atom and being optionally substituted with one to three $C_1$-$C_3$ alkyl groups optionally substituted with one OH, oxo, aryl, or —$NR^aR^b$;
$R^4$ is H, halo, $C_1$-$C_3$ alkyl, $C_1$-$C_3$ haloalkyl, cyano, $C_1$-$C_3$ alkoxy, $NR^aR^b$, aryl optionally substituted with one to three $R^5$, or heteroaryl optionally substituted with one to three $R^6$;
each $R^5$ is independently selected from the group consisting of halo, CN, $C_1$-$C_3$ alkoxy, heteroaryl, —$S(O)_2R^a$, —$S(O)_2NR^aR^b$, —$NR^aS(O)_2Ra$, —$NR^bC(O)R^a$, —$C(O)NR^aR^b$, —$NR^bC(O)NR^aR^b$, and $C_1$-$C_3$ alkyl optionally substituted by —$NR^aR^b$;
each $R^6$ is independently selected from the group consisting of OH, —$NR^aR^b$, —$NR^bC(O)R^a$, 1,1-cyclopropanedicarboxamide, heteroaryl, heterocycloalkyl, and aryl optionally substituted by $S(O)_2NH_2$;

each $R^7$ is independently selected from the group consisting of OH, $C_1$-$C_3$ alkoxy, —$NR^aR^b$, and $C_1$-$C_3$ alkyl optionally substituted by —$NR^aR^b$;
each $R^a$ is independently selected from the group consisting of H, heterocycloalkyl, and $C_1$-$C_3$ alkyl optionally substituted with one —$NH_2$ or $NHCH_3$; and
each $R^b$ is independently H or $C_1$-$C_6$ alkyl.

In one embodiment of the present invention $R^1$ is optionally substituted aryl, suitably phenyl optionally substituted with one to three $R^5$ groups. Specifically $R^1$ is phenyl optionally substituent with one to three $R^5$ wherein $R^5$ is fluoro, CN, —$S(O)_2R^a$, —$S(O)_2NR^aR^b$, —$NR^bC(O)R^a$, and $C_1$-$C_3$ alkyl optionally substituted by —$NR^aR^b$. Suitably $R^1$ is —$CH_2$-phenyl optionally substituted with one to three $R^5$. Suitably $R^1$ is pyrazolyl or indazolyl optionally substituted with one to three $R^5$.

In another embodiment of the present invention $R^2$ is H, $C_1$-$C_6$ alkyl optionally substituted with one or two $R^6$, $C_3$-$C_6$ cycloalkyl optionally substituted with one to three $R^7$, or heterocycloalkyl optionally substituted with one to three $R^7$; and $R^3$ is H, $C_1$-$C_6$ alkyl, or phenyl. Suitably $R^2$ is $C_1$-$C_6$ alkyl optionally substituted with one or two $R^6$. In another embodiment $R^2$ is pyrrolidinyl, piperidinyl, cyclohexyl, or cyclopropyl each of which is optionally substituted with one to three $R^7$; and $R^3$ is H, $C_1$-$C_6$ alkyl, or phenyl.

In another embodiment of the present invention $R^4$ is H, methyl, or bromo.

Examples of the present invention include:

2-[(3-aminopropyl)amino]-4-[(3-methylphenyl)amino]pyrido[4,3-d]pyrimidin-5(6H)-one;

2-[(3-aminopropyl)amino]-4-[(phenylmethyl)amino]pyrido[4,3-d]pyrimidin-5(6H)-one;

2-[(3-aminopropyl)amino]-4-(phenylamino)pyrido[4,3-d]pyrimidin-5(6H)-one;

2-[(3-aminopropyl)amino]-4-[(2-fluorophenyl)amino]pyrido[4,3-d]pyrimidin-5(6H)-one;

2-[(3-aminopropyl)amino]-8-methyl-4-[(3-methylphenyl)amino]pyrido[4,3-d]pyrimidin-5(6H)-one;

2-[(3-aminopropyl)amino]-4-{[4-(methylsulfonyl)phenyl]amino}pyrido[4,3-d]pyrimidin-5(6H)-one;

2-[(3-aminopropyl)amino]-4-{[3-(methylsulfonyl)phenyl]amino}pyrido[4,3-d]pyrimidin-5(6H)-one;

2-[(3-aminopropyl)amino]-4-{[3-(3-aminopropyl)phenyl]amino}pyrido[4,3-d]pyrimidin-5(6H)-one;

4-{[3-(2-aminoethyl)phenyl]amino}-2-[(3-aminopropyl)amino]pyrido[4,3-d]pyrimidin-5(6H)-one;

4-{[4-(2-aminoethyl)phenyl]amino}-2-[(3-aminopropyl)amino]pyrido[4,3-d]pyrimidin-5(6H)-one;

2-[(3-aminopropyl)amino]-8-methyl-4-[(3-methylphenyl)amino]pyrido[4,3-d]pyrimidin-5(6H)-one;

4-(1H-pyrazol-4-ylamino)-2-[(3R)-3-pyrrolidinylamino]pyrido[4,3-d]pyrimidin-5(6H)-one;

2-[(3-aminopropyl)amino]-4-[(2-methylphenyl)amino]pyrido[4,3-d]pyrimidin-5(6H)-one;

2-[(3-aminopropyl)amino]-4-[(2,2-dioxido-1,3-dihydro-2-benzothien-5-yl)amino]pyrido[4,3-d]pyrimidin-5(6H)-one;

N-[3-({2-[(3-aminopropyl)amino]-5-oxo-5,6-dihydropyrido[4,3-d]pyrimidin-4-yl}amino)phenyl]-1-pyrrolidinecarboxamide;

N-{3-[(2-{[2-(1H-imidazol-4-yl)ethyl]amino}-5-oxo-5,6-dihydropyrido[4,3-d]pyrimidin-4-yl)amino]phenyl}-1-pyrrolidinecarboxamide;

N-[3-({5-oxo-2-[(3R)-3-pyrrolidinylamino]-5,6-dihydropyrido[4,3-d]pyrimidin-4-yl}amino)phenyl]-1-pyrrolidinecarboxamide;

N-[4-({2-[(3-aminopropyl)amino]-5-oxo-5,6-dihydropyrido[4,3-d]pyrimidin-4-yl}amino)phenyl]-1-pyrrolidinecarboxamide;

3-({2-[(3-aminopropyl)amino]-5-oxo-5,6-dihydropyrido[4,3-d]pyrimidin-4-yl}amino)-N-ethylbenzenesulfonamide;

2-[(3-aminopropyl)amino]-4-(1H-indazol-6-ylamino)pyrido[4,3-d]pyrimidin-5(6H)-one;

2-[(3-aminopropyl)amino]-4-(1H-indazol-5-ylamino)pyrido[4,3-d]pyrimidin-5(6H)-one;

4-({2-[(3-aminopropyl)amino]-5-oxo-5,6-dihydropyrido[4,3-d]pyrimidin-4-yl}amino)benzonitrile;

2-[(3-aminopropyl)amino]-8-bromo-4-[(3-methylphenyl)amino]pyrido[4,3-d]pyrimidin-5(6H)-one;

2-{[3-(dimethylamino)propyl]amino}-4-[(3-methylphenyl)amino]pyrido[4,3-d]pyrimidin-5(6H)-one;

2-[[3-(dimethylamino)propyl](methyl)amino]-4-[(3-methylphenyl)amino]pyrido[4,3-d]pyrimidin-5(6H)-one;

2-{[3-(methylamino)propyl]amino}-4-[(3-methylphenyl)amino]pyrido[4,3-d]pyrimidin-5(6H)-one;

4-[(3-methylphenyl)amino]-2-{[3-(4-morpholinyl)propyl]amino}pyrido[4,3-d]pyrimidin-5(6H)-one;

4-[(3-methylphenyl)amino]-2-{[2-(4-pyridinyl)ethyl]amino}pyrido[4,3-d]pyrimidin-5(6H)-one;

4-[(3-methylphenyl)amino]-2-[(1-methyl-4-piperidinyl)amino]pyrido[4,3-d]pyrimidin-5(6H)-one;

4-[2-({4-[(3-methylphenyl)amino]-5-oxo-5,6-dihydropyrido[4,3-d]pyrimidin-2-yl}amino)ethyl]benzenesulfonamide;

2-{[2-(1H-imidazol-2-yl)ethyl]amino}-4-[(3-methylphenyl)amino]pyrido[4,3-d]pyrimidin-5(6H)-one;

2-[(4-aminocyclohexyl)amino]-4-[(3-methylphenyl)amino]pyrido[4,3-d]pyrimidin-5(6H)-one;

2-[(3-aminocyclohexyl)amino]-4-[(3-methylphenyl)amino]pyrido[4,3-d]pyrimidin-5(6H)-one;

2-[(3-amino-2,2-dimethylpropyl)amino]-4-[(3-methylphenyl)amino]pyrido[4,3-d]pyrimidin-5(6H)-one;

4-[(3-methylphenyl)amino]-2-{[3-(2-oxo-1-pyrrolidinyl)propyl]amino}pyrido[4,3-d]pyrimidin-5(6H)-one;

2-[(2-amino-2-methylpropyl)amino]-4-[(3-methylphenyl)amino]pyrido[4,3-d]pyrimidin-5(6H)-one;

2-(methylamino)-4-[(3-methylphenyl)amino]pyrido[4,3-d]pyrimidin-5(6H)-one;

2-amino-4-[(3-methylphenyl)amino]pyrido[4,3-d]pyrimidin-5(6H)-one;

2-[(3-amino-2-hydroxypropyl)amino]-4-[(3-methylphenyl)amino]pyrido[4,3-d]pyrimidin-5(6H)-one;

2-(cyclopropylamino)-4-[(3-methylphenyl)amino]pyrido[4,3-d]pyrimidin-5(6H)-one;

4-[(3-methylphenyl)amino]-2-(4-piperidinylamino)pyrido[4,3-d]pyrimidin-5(6H)-one;

4-[(3-methylphenyl)amino]-2-{[2-(1-piperazinyl)ethyl]amino}pyrido[4,3-d]pyrimidin-5(6H)-one;

4-[(3-methylphenyl)amino]-2-[(4-piperidinylmethyl)amino]pyrido[4,3-d]pyrimidin-5(6H)-one;

4-[(3-methylphenyl)amino]-2-[(3S)-3-pyrrolidinylamino]pyrido[4,3-d]pyrimidin-5(6H)-one;

4-[(3-methylphenyl)amino]-2-[(3R)-3-piperidinylamino]pyrido[4,3-d]pyrimidin-5(6H)-one;

2-[4-(aminomethyl)-1-piperidinyl]-4-[(3-methylphenyl)amino]pyrido[4,3-d]pyrimidin-5(6H)-one;

2-[(3R)-3-amino-1-pyrrolidinyl]-4-[(3-methylphenyl)amino]pyrido[4,3-d]pyrimidin-5(6H)-one;

2-[(3S)-3-amino-1-pyrrolidinyl]-4-[(3-methylphenyl)amino]pyrido[4,3-d]pyrimidin-5(6H)-one;

4-[(3-methylphenyl)amino]-2-[(3R)-3-pyrrolidinylamino]pyrido[4,3-d]pyrimidin-5(6H)-one;

4-[(3-methylphenyl)amino]-2-[(3R)-3-piperidinylamino]pyrido[4,3-d]pyrimidin-5(6H)-one;

$N^1$-[3-({4-[(3-methylphenyl)amino]-5-oxo-5,6-dihydropyrido[4,3-d]pyrimidin-2-yl}amino)propyl]-1,1-cyclopropanedicarboxamide;

(4R)—N-[3-({4-[(3-methyl phenyl)amino]-5-oxo-5,6-dihydropyrido[4,3-d]pyrimidin-2-yl}amino)propyl]-2-oxo-1,3-thiazolidine-4-carboxamide;

$N^2$-methyl-$N^1$-[3-({4-[(3-methylphenyl)amino]-5-oxo-5,6-dihydropyrido[4,3-d]pyrimidin-2-yl}amino)propyl]glycinamide; and N-[3-({4-[(3-methylphenyl)amino]-5-oxo-5,6-dihydropyrido[4,3-d]pyrimidin-2-yl}amino)propyl]-L-prolinamide.

The skilled artisan will appreciate that pharmaceutically-acceptable salts of the compounds according to Formula I may be prepared. Indeed, in certain embodiments of the invention, pharmaceutically-acceptable salts of the compounds according to Formula I may be preferred over the respective free base because such salts impart greater stability or solubility to the molecule thereby facilitating formulation into a dosage form. Accordingly, the invention is further directed to pharmaceutically-acceptable salts of the compounds according to Formula I.

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass all individual stereoisomers and all mixtures thereof. Thus, compounds according to Formula I containing one or more chiral center may be used as racemic mixtures, enantiomerically enriched mixtures, or as enantiomerically pure individual stereoisomers.

Individual stereoisomers of a compound according to Formula I which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

The compounds of Formula I or pharmaceutically-acceptable salts thereof may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing vaiable amounts of water. The invention includes all such solvates.

The skilled artisan will further appreciate that certain compounds of Formula I or pharmaceutically-acceptable salts thereof that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

"Alkyl" refers to a saturated hydrocarbon chain having the specified number of member atoms. For example, $C_1$-$C_6$ alkyl refers to an alkyl group having from 1 to 6 member atoms. Alkyl groups may be optionally substituted with one or more substituents as defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Alkoxy" refers to an O—$C_1$-$C_6$ alkyl group wherein $C_1$-$C_6$ alkyl is as defined herein. Examples of such groups include methoxy, ethoxy, propoxy, butoxy, pentoxy and hexoxy.

"Aryl and Ar" refers to an aromatic hydrocarbon ring. Aryl groups are monocyclic ring systems or bicyclic ring systems. Monocyclic aryl ring refers to phenyl. Bicyclic aryl rings refer to napthyl and rings wherein phenyl is fused to a cycloalkyl or cycloalkenyl ring having 5, 6, or 7 member atoms. Aryl groups may be optionally substituted with one or more substituents as defined herein.

"Cycloalkyl" refers to a saturated hydrocarbon ring having the specified number of member atoms. Cycloalkyl groups are monocyclic ring systems. For example, $C_3$-$C_6$ cycloalkyl refers to a cycloalkyl group having from 3 to 6 member atoms. Cycloalkyl groups may be optionally substituted with one or more substituents as defined herein. Cycloalkyl includes cyclopropyl, cyclobutyl, cyclopentyl, and cyclohexyl.

"Halo" refers to the halogen radicals fluoro, chloro, bromo, and iodo.

"Haloalkyl" refers to an alkyl group wherein at least one hydrogen atom attached to a member atom within the alkyl group is replaced with halo. Haloalkyl includes monofluoromethyl, difluoroethyl, and trifluoromethyl.

"Heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituents as defined herein. Heteroaryl groups are monocyclic ring systems or are fused, spiro, or bridged bicyclic ring systems. Monocyclic heteroaryl rings have 5 or 6 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benopyranyl, benzoxazolyl, benzofuranyl, isobenzofuranyl, benzothiazolyl, benzothienyl, furopyridinyl, and napthyridinyl.

"Heteroatom" refers to a nitrogen, sulphur, or oxygen atom.

"Heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituents as defined herein. Heterocycloalkyl groups are monocyclic ring systems having from 4 to 7 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, and azetidinyl.

"Optionally substituted" indicates that a group, such as alkyl, alkenyl, alkynyl, aryl, cycloalkyl, cycloalkenyl, heterocycloalkyl, or heteroaryl, may be unsubstituted or substituted with one or more substituents as defined herein. "Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Ac (acetyl); ATP (adenosine triphosphate);
BBDM (tert-butoxy bis(dimethylamino)methane);
BOC (tert-butyloxycarbonyl); BSA (bovine serum albumin);
$CH_3CN$ (acetonitrile); DCM (dichloromethane);
DIEA (N,N-Diisopropylethylamine); DIPEA (diisopropylethylamine);
DMA (dimethylacetamide); DMF (N,N-dimethylformamide);
DMSO (dimethylsulfoxide);
EDC (1-[3-dimethylamino)propyl]-3-ethylcarbodiimide hydrochloride);
EDTA (ethylenediaminetetraacetic acid);
EtOAc (ethyl acetate);
HATU (O-(7azabenzobenzotriazol-1-yl)-N,N,N',N'-tetramethyluronium hexafluorophosphate);
HEPES (4-(2-hydroxyethyl)-1-piperazine ethane sulfonic acid);
HOAc (acetic acid);
HOBT (1-hydroxybenzotriazole);
HPLC (high pressure liquid chromatography);
LHMDS (lithium hexamethyldisilazide)
mCPBA (meta-chloroperbenzoic acid);
MeOH (methanol);
NBS (N-bromosuccinimide);
TFA ((trifluoroacetic acid); and
THF (tetrahydrofuran).

Compound Preparation

The compounds according to Formula I are prepared using conventional organic syntheses. A suitable synthetic route is depicted below in the following general reaction schemes.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

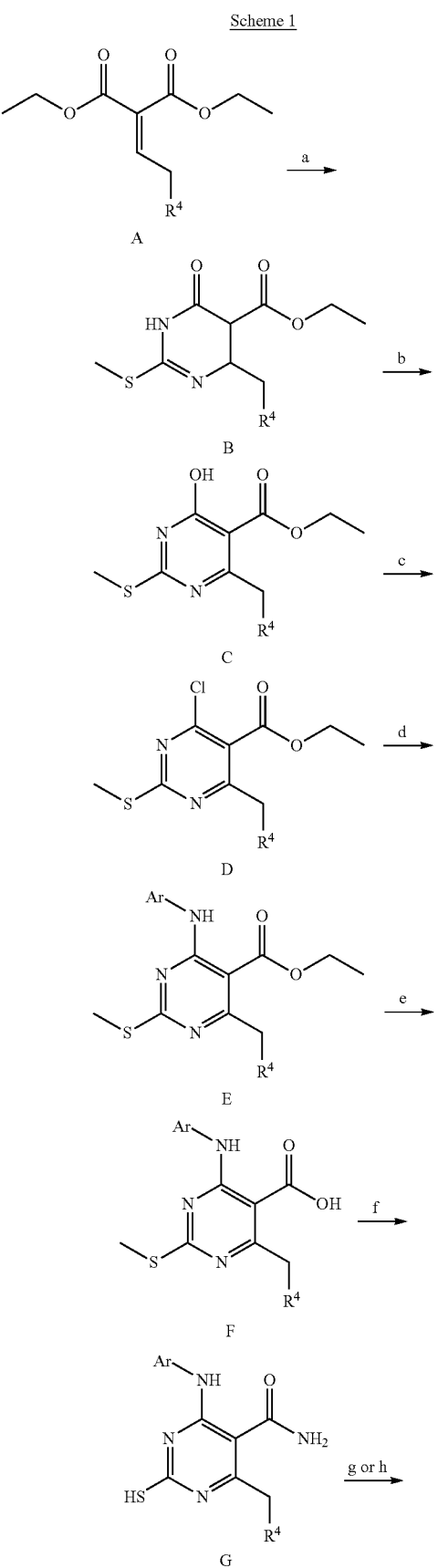

Scheme 1

-continued

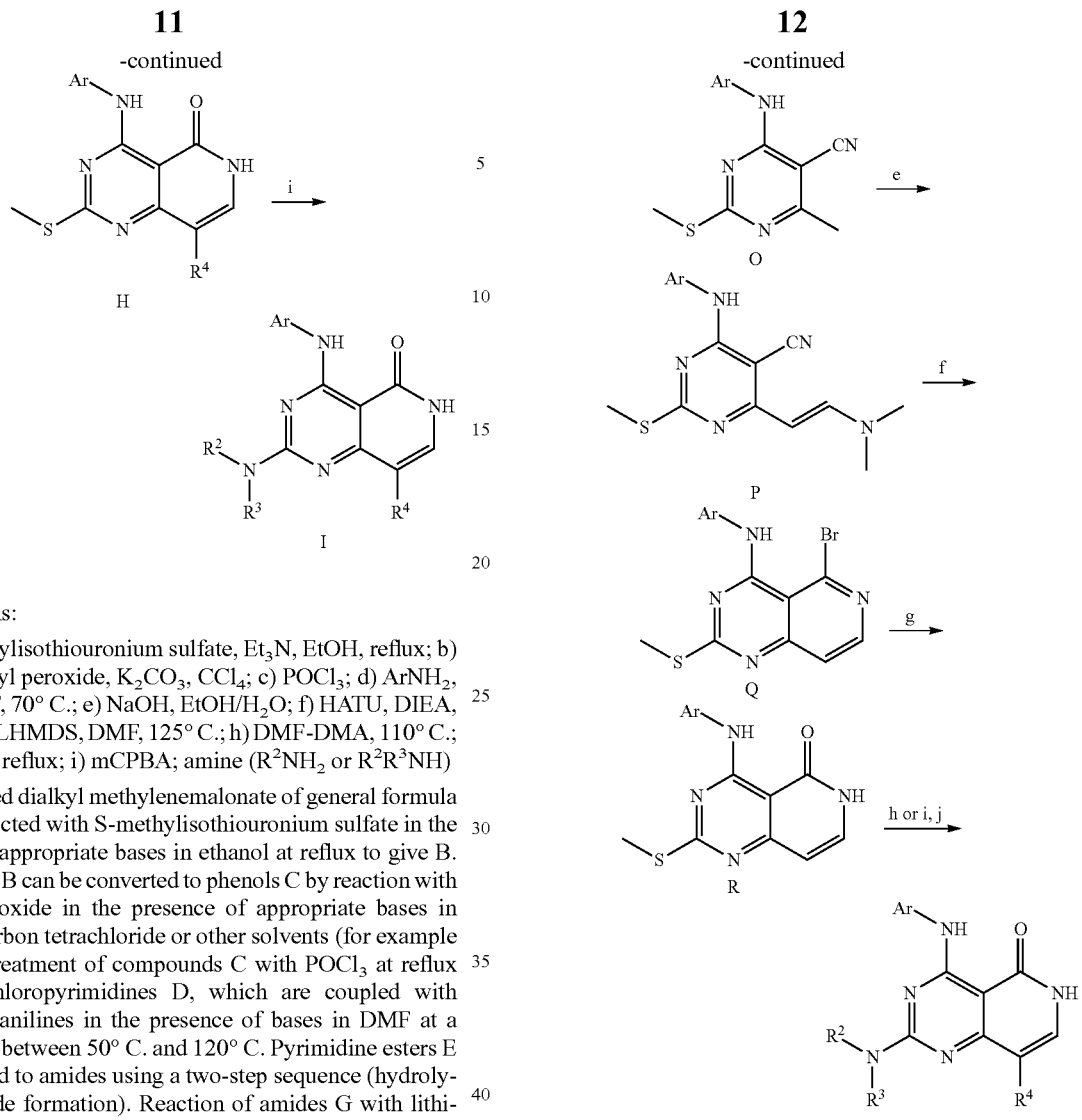

Conditions:

a) S-methylisothiouronium sulfate, Et₃N, EtOH, reflux; b) NBS, benzoyl peroxide, K₂CO₃, CCl₄; c) POCl₃; d) ArNH₂, DIEA, DMF, 70° C.; e) NaOH, EtOH/H₂O; f) HATU, DIEA, NH₄OH; g) LHMDS, DMF, 125° C.; h) DMF-DMA, 110° C.; then HOAc, reflux; i) mCPBA; amine (R²NH₂ or R²R³NH)

Substituted dialkyl methylenemalonate of general formula A can be reacted with S-methylisothiouronium sulfate in the presence of appropriate bases in ethanol at reflux to give B. Compounds B can be converted to phenols C by reaction with benzoyl peroxide in the presence of appropriate bases in refluxing carbon tetrachloride or other solvents (for example dioxane). Treatment of compounds C with POCl₃ at reflux produces chloropyrimidines D, which are coupled with appropriate anilines in the presence of bases in DMF at a temperature between 50° C. and 120° C. Pyrimidine esters E are converted to amides using a two-step sequence (hydrolysis and amide formation). Reaction of amides G with lithiumhexamethyldisilazane in DMF at a temperature between 100° C. and 140° C. gives pyrido[4,3-d]pyrimidin-5(6H)-one derivatives H. Alternatively, compounds H can be prepared by reaction of compounds G with DMF-DMA in DMF at a temperature between 80° C. and 120° C. followed by refluxing the resulting enamine in acetic acid. Oxidation of the sulfide of compounds H with oxidation reagents (i.e. mCPBA, H₂O₂-TFA) followed by displacement of the sulfone with appropriate amines and deprotection produce desired pyrimidopyridone analogs I.

Scheme 2

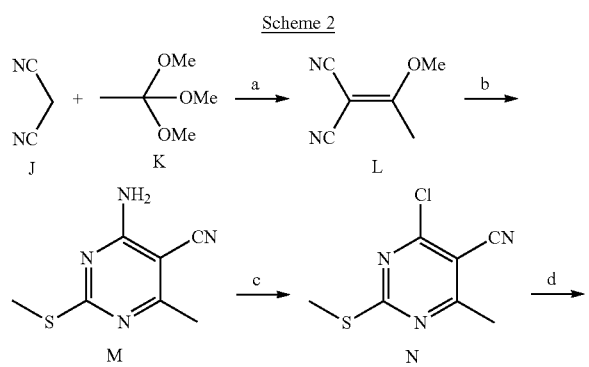

Conditions:

a) acetic acid, 90° C. to 140° C.; b) S-methylisothiouronium sulfate, NaOMe, CH₃OH; c) CuCl₂, tert-butylnitrite, MgSO₄, acetonitrile, 80° C.; d) ArNH₂, DIEA, DMF, 75° C.; or ArNH₂, conc. HCl, isopropanol, reflux; or TsOH, 1,4-dixoane, 90° C.; e) DMF-DMA or tert-butoxy bis(dimethylamino)methane (BBDM), DMF, 110° C.; f) 33% HBr/HOAc; g) 6N HCl (aq.)/HOAc, 80° C.; h) mCPBA, DMF; then amine (R²R³NH); i) mCPBA, DMF, Boc-protected amine; j) TFA, CH₂Cl₂.

As shown in Scheme 2, 4-amino-6-methyl-2-(methylthio)-5-pyrimidinecarbonitrile (M) can be prepared by condensing malononitrile (J) and triethyl orthoacetate (K) and reacting the resulting (1-ethoxyethylidene)malononitrile (L) and s-methylisothiourea hemisulfate salt in methanol.

Compounds M may be halogenated by reaction of the amino functional group in the presence of a diazotizing reagent and a cupric halide, for example tert-butylnitrite and cupric chloride, to give N. Compounds N may be reacted with anilines or heteroaryl amines to provide compound O either in the presence of appropriate bases (for example N,N-diisopropylethylamine), in DMF at a temperature between 65° C. and 120° C., or in the presence of concentrated hydrochloride acid in isopropanol at reflux, or in the presence of TsOH in 1,4- dioxane at 90° C. Treatment of compounds O with either DMF-DMA or tert-butoxy bis(dimethylamino)methane (BBDM) in DMF at a temperature between 90° C. to 120° C. affords the enamines P. Reaction of P with a solution of 33% HBr in acetic acid produces the brominated compounds Q, which are hydrolyzed to R using 6N HCl aqueous solution in acetic acid a temperature between 60° C. to 100° C. Oxidation of the sulfides R with a suitable reagent, for example mCPBA or $H_2O_2$/TFA, and displacement of the resulting sulfone with appropriate amines and deprotection (if necessary) afford desired pyrido[4,3-d]pyrimidin-5(6H)-one derivatives I, where $R^4$=H.

Methods of Use

The compounds according to Formula I and pharmaceutically acceptable salts thereof are inhibitors of PDK1. These compounds are potentially useful in the treatment of conditions wherein the underlying pathology is attributable to (but not limited to) constitutively activated ACG kinases, for example, cancer and more specifically cancers of the breast, colon, and lung. What is meant by constitutively activated ACG kinases is that one or more ACG kinases are being produced at a constant rate regardless of physiological demand or concentration. Accordingly, in another aspect the invention is directed to methods of treating such conditions.

Suitably, the present invention relates to a method for treating or lessening the severity of breast cancer, including inflammatory breast cancer, ductal carcinoma, and lobular carcinoma.

Suitably the present invention relates to a method for treating or lessening the severity of colon cancer.

Suitably the present invention relates to a method for treating or lessening the severity of lung cancer including small cell lung cancer, non-small cell lung cancer, squamous cell carcinoma, adenocarcinoma, and large cell carcinoma.

Suitably the present invention relates to a method for treating or lessening the severity of cancers selected from the group consisting of brain (gliomas), glioblastomas, Wilm's tumor, Ewing's sarcoma, Rhabdomyosarcoma, ependymoma, medulloblastoma, head and neck, kidney, liver, melanoma, ovarian, pancreatic, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

The methods of treatment of the invention comprise administering a safe and effective amount of a compound according to Formula I or a pharmaceutically-acceptable salt thereof to a patient in need thereof.

The invention also provides a compound according to Formula I or a pharmaceutically-acceptable salt thereof for use in medical therapy, and particularly in cancer therapy. Thus, in further aspect, the invention is directed to the use of a compound according to Formula I or a pharmaceutically-acceptable salt thereof in the preparation of a medicament for the treatment of a disorder characterized by constitutively activated ACG kinases, such as cancer.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "patient" refers to a human or other animal.

The compounds of Formula I or pharmaceutically-acceptable salts thereof may be administered by any suitable route of administration, including systemic administration. Systemic administration includes oral administration, and parenteral administration, Parenteral administration refers to routes of administration other than enteral, transdermal, or by inhalation, and is typically by injection or infusion. Parenteral administration includes intravenous, intramuscular, and subcutaneous injection or infusion.

The compounds of Formula I or pharmaceutically-acceptable salts thereof may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Additionally, the compounds of Formula I or pharmaceutically-acceptable salts thereof may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound.

Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The compounds of Formula I and pharmaceutically acceptable salts thereof may be co-administered with at least one other active ingredient known to be useful in the treatment of cancer.

By the term "co-administration" as used herein is meant either simultaneous administration or any manner of separate sequential administration of an PDK1 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered by injection and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients (anti-neoplastic agent) for use in combination or co-administered with the presently invented PDK1 inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)—O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside] is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

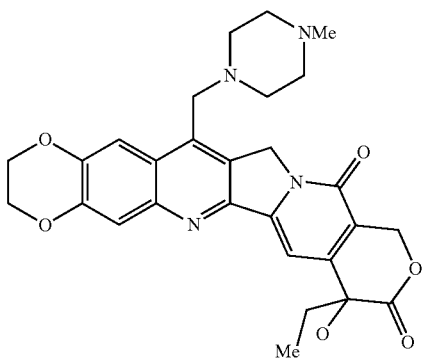

known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidylinositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-lacaci, L., et al, Int. J. Cancer (2000), 88(1), 44-52.

Inhibitors of Phosphotidyl inositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen Let al. (2000), Oncogene 19: 3460-3469).

Agents used in immunotherapeutic regimens may also be useful in combination with the compounds of formula (I). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to down-regulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

Compositions

The compounds of Formula I or pharmaceutically-acceptable salts thereof will normally, but not necessarily, be formulated into pharmaceutical compositions prior to administration to a patient. Accordingly, in another aspect the invention is directed to pharmaceutical compositions comprising a compounds of Formula I or pharmaceutically acceptable salts thereof and one or more pharmaceutically-acceptable excipient.

The pharmaceutical compositions of the invention may be prepared and packaged in bulk form wherein a safe and effective amount of a compound of Formula I or pharmaceutically acceptable salt thereof can be extracted and then given to the patient such as with powders or syrups. Alternatively, the pharmaceutical compositions of the invention may be prepared and packaged in unit dosage form wherein each physically discrete unit contains a safe and effective amount of a compound of Formula I or pharmaceutically acceptable salt thereof. When prepared in unit dosage form, the pharmaceutical compositions of the invention typically may contain, for example, from 0.5 mg to 1 g, or from 1 mg to 700 mg, or from 5 mg to 100 mg of a compound of the invention.

The pharmaceutical compositions of the invention typically contain one compound of Formula I or pharmaceutically acceptable salt thereof. However, in certain embodiments, the pharmaceutical compositions of the invention contain more than one compound of Formula I. For example, in certain embodiments the pharmaceutical compositions of the invention contain two compounds of Formula I. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of Formula I or pharmaceutically acceptable salt thereof and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; and (2) parenteral administration such as sterile solutions, suspensions, and powders for reconstitution;

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in Remington's *Pharmaceutical Sciences* (Mack Publishing Company).

In one aspect, the invention is directed to a solid oral dosage form such as a tablet or capsule comprising a safe and effective amount of a compound of Formula I or pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of the invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of the invention. Syrups can be prepared by dissolving the compound of the invention in a suitably flavored aqueous solution, while elixirs are prepared through the use of a non-toxic alcoholic vehicle. Suspensions can be formulated by dispersing the compound of the invention in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Other pharmaceutically-acceptable excipients may be added to the suspension or solution. The compound of the invention may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

Another aspect of the invention is directed to a pharmaceutical composition adapted for parenteral administration comprising a compound of Formula I or a pharmaceutically acceptable salt thereof. Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Instrumentation:

| LC-MS: | Instrumentation |
|---|---|
| LC: | Shimadzu 10A (controller, pumps, and UV detector) |
| UV: | Shimadzu 10A (214 nm) |
| ELS: | Sedere Sedex 75C |
| MS: | PE Sciex Single Quadrupole 100LC, 150EX, or Waters ZQ Polarity (positive); Mode (profile); Scan Time (0.33 s); Step (0.2 m/z) Capillary V (5500); Cone V (25-45); |
| Autosampler: | CTC Leap; 3 uL loop; default injection volume = 2 uL (default) |
| Column: | Thermo Hypersil Gold (C18, 20 × 2.1 mm, 1.9 u particle diam.) |
| Heater: | Phenomenex 45° C. |
| Solvent A: | H$_2$O, 0.02% TFA |
| Solvent B: | MeCN, 0.018% TFA |
| Gradient: | Time (min) | Flow (mL/min) | Sol. B |
|  | 0.02 | 1.6 | 4.0 |
|  | 1.90 |  | 92.0 |
|  | 1.91 |  | 4.0 |
|  | 2.00 | Stop |  |

HPLC conditions:
Solvent A: 0.1% TFA/H$_2$O
Solvent B: 0.1% TFA/CH$_3$CN
Columns:
Luna 5 u C18(2) 100 A AXIA 50 × 30 mm 5 micron preparatory column
Luna 5 u C18(2) 100 A, AXIA. 50 × 21.20 mm 5 micron preparatory column
UV detection at 254 nm.

Intermediate 1

Ethyl 4-methyl-2-(methylthio)-6-oxo-1,4,5,6-tetrahydro-5-pyrimidinecarboxylate

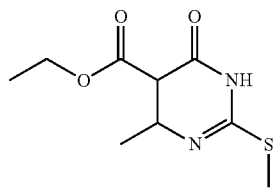

A round bottom flask was charged with S-methylisothiouronium sulfate (14.0 g, 100.6 mmol), diethyl ethylidene malonate (18.7 g, 100.6 mmol), triethylamine (20.4 g, 201.2 mmol) and ethanol (200 mL). The flask was fitted with a reflux condenser and the reaction was heated to reflux for 20 h. The reaction was cooled to room temperature and ethanol was removed under vacuum. The residue was dissolved into ethyl acetate (200 mL) and the solution was washed with water, brine, and dried over MgSO$_4$, filtered and evaporated to afford the product (12.2 g, 87% yield).

MS: M(C$_9$H$_{14}$N$_2$O$_3$S$_1$)=230.29, (M+H)$^+$=231.0.

$^1$H NMR (400 MHz, CDCl$_3$) δ ppm 1.07-1.36 (m, 6H), 2.23-2.46 (m, 3H), 2.98-3.38 (m, 1H), 3.90-4.45 (m, 3H) 8.61 (br. s, 1H).

Intermediate 2

Ethyl 4-methyl-2-(methylthio)-6-oxo-1,6-dihydro-5-pyrimidinecarboxylate

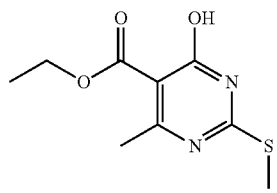

A round bottom flask was charged with ethyl 4-methyl-2-(methylthio)-6-oxo-1,4,5,6-tetrahydro-5-pyrimidinecarboxylate (11.2 g, 48.7 mmol), N-bromo succinimide (8.67 g, 48.7 mmol), benzoyl peroxide (0.65 g, 2.7 mmol), potassium carbonate (67 g, 487 mmol) and carbon tetrachloride (700 mL). The reaction was heated to reflux for 45 min and cooled to room temperature. The reaction was quenched with to water (500 mL) and washed with methylene chloride. Aqueous phase was acidified by dropwise addition of conc. HCl and extracted with methylene chloride. The extract was dried over MgSO$_4$, filtered, and evaporated under vacuum to afford the product (8.2 g, 78% yield).

MS: M(C$_9$H$_{12}$N$_2$O$_3$S$_1$)=228.27, (M+H)$^+$=228.9.

$^1$H NMR (400 MHz, CDCl$_3$) δ ppm 1.43 (t, J=7.2 Hz, 3H) 2.58 (s, 3H) 2.59 (s, 3H) 4.44 (q, J=7.1 Hz, 2H) 12.46 (br. s., 1H)

Intermediate 3

Ethyl 4-chloro-6-methyl-2-(methylthio)-5-pyrimidinecarboxylate

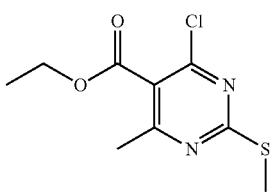

A round bottom flask was charged with ethyl 4-methyl-2-(methylthio)-6-oxo-1,6-dihydro-5-pyrimidinecarboxylate (6 g) and phosphorus oxychloride (30 mL) and heated to reflux for 3 h. The phosphorus oxychloride was removed under vacuum. The residue was chromatographed (silica gel, eluting with methylene chloride) to afford the product (5.73 g, 87% yield).

MS: $M(C_9H_{11}C_{11}N_2O_2S_1)=246.72$, $(M+H)^+=246.8$.

$^1H$ NMR (400 MHz, CDCl$_3$) δ ppm 1.41 (t, J=7.2 Hz, 3H), 2.50 (s, 3H), 2.57 (s, 3H), 4.44 (q, J=7.2 Hz, 2H).

Intermediate 4

Ethyl 4-methyl-6-[(3-methylphenyl)amino]-2-(methylthio)-5-pyrimidinecarboxylate

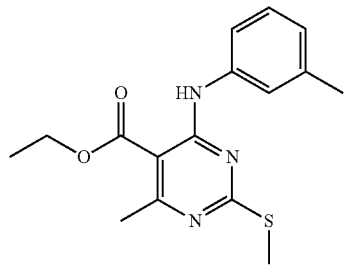 [SMILES: CCOC(=O)c1c(C)nc(SC)nc1Nc1cccc(C)c1]

A round bottom flask was charged with ethyl 4-methyl-6-[(3-methylphenyl)amino]-2-(methylthio)-5-pyrimidinecarboxylate (2.5 g, 10.13 mmol), diisopropyl ethyl amine (2.88 g, 22.3 mmol), 3-methylaniline (1.19 g, 11.14 mmol) and dimethylformamide (40 mL). The reaction was heated at 70° with stirring overnight. The solvent was evaporated under vacuum. The residue was dissolved into ethyl acetate (100 mL) and the solution was washed with water, brine, dried over MgSO$_4$, filtered, and evaporated. This material was chromatographed (silica gel, eluting with hexane to methylene chloride gradient) to afford the product (2.83 g, 75% yield)

MS: $M(C_{16}H_{19}N_3O_2S_1)=317.41$, $(M+H)^+=318.1$.

$^1H$ NMR (400 MHz, CDCl$_3$) δ ppm 1.43 (t, J=7.2 Hz, 3H), 2.36 (s, 3H), 2.52 (s, 3H), 2.64 (s, 3H), 4.40 (q, J=7.07 Hz, 2H), 6.94 (d, J=7.3 Hz, 1H), 7.19-7.32 (m, 1H), 7.41-7.57 (m, 2H), 10.57 (br. s, 1H).

Intermediate 5

4-methyl-6-[(3-methylphenyl)amino]-2-(methylthio)-5-pyrimidinecarboxylic acid

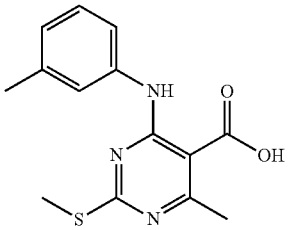 [SMILES: CSc1nc(C)c(C(=O)O)c(Nc2cccc(C)c2)n1]

To a 100 ml round-bottom flask were added ethyl 4-methyl-6-[(3-methylphenyl)amino]-2-(methylthio)-5-pyrimidinecarboxylate (2.83 g, 8.92 mmole), sodium hydroxide (dissolved in 5 mL of water) (0.53 g, 13.4 mmole), ethanol (25 mL) and water (25 mL). The reaction was stirred at reflux for 2 h. It was cooled to room temperature and concentrated under vacuum. The residue was treated with water (100 mL) and acidified by dropwise addition of acetic acid. Ethyl acetate (500 mL) was then added and the mixture was stirred for 10 min. The organic phase was separated. The aqueous phase was extracted with ethyl acetate (2×) and the organic extracts were combined and washed with water, brine and dried over MgSO$_4$. The solvent was removed under vacuum to yield the product (2.6 g).

Alternate workup: after acidification of aqueous phase with acetic acid the precipitated product was filtered off and dried in vacuum oven.

MS: $M(C_{14}H_{16}N_3O_2S_1)=289.36$, $(M+H)^+=289.7$

1H NMR (400 MHz, DMSO-d$_6$) δ ppm 1.92 (s, 3H), 2.31 (s, 3H), 2.47 (s, 3H), 6.93 (d, J=7.3 Hz, 1H), 7.24 (t, J=7.8 Hz, 1H), 7.42 (s, 1H), 7.50 (s, 1H), 10.69 (s, 1H), 11.32-14.57 (m, 1H).

Intermediate 6

4-methyl-6-[(3-methylphenyl)amino]-2-(methylthio)-5-pyrimidinecarboxamide

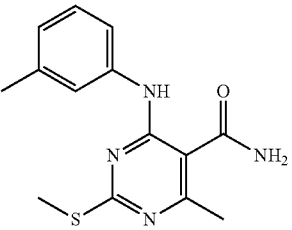 [SMILES: CSc1nc(C)c(C(N)=O)c(Nc2cccc(C)c2)n1]

To a solution of 4-methyl-6-[(3-methylphenyl)amino]-2-(methylthio)-5-pyrimidinecarboxylic acid (1.71 g, 5.90 mmole) in DMF (40 mL) were added o-(7-azabenzotriazol-1-yl)-N,N,N,N-tetramethyl uroniumhexafluoro phosphate (4.88 g, 12.8 mmole) and diisopropylethylamine (3.83 g, 29.6 mmole). The reaction mixture was stirred for 10 min before ammonium hydroxide (7.2 ml of 28%) was added. The mixture was stirred for additional 20 min and DMF was removed under vacuum. The residue was partitioned between ethyl acetate and water. The insoluble product was collected by filtration and dried under vacuum (0.54 g). The organic phase was separated, washed with 1N NaOH, water and dried over MgSO$_4$. The solvent was removed under vacuum to give additional product (1.03 g) which was combined with the previously obtained precipitated product (1.27 g in total, 74% yield).

MS: M(C₁₄H₁₆N₄O₁S₁)=288.37, (M+H)⁺=288.7

1H NMR (400 MHz, DMSO-d₆) δ ppm 2.29 (s, 3H), 2.39 (s, 3H), 2.46 (s, 3H), 6.88 (d, J=7.6 Hz, 1H), 7.21 (t, J=7.8 Hz, 1H), 7.41 (d, J=7.8 Hz, 1H), 7.48 (s, 1H), 7.88 (br. s, 1H), 7.99 (br. s, 1H), 9.16 (s, 1H).

Intermediate 7

4-[(3-methylphenyl)amino]-2-(methylthio)pyrido[4,3-d]pyrimidin-5(6H)-one

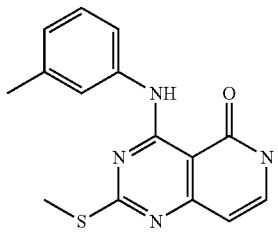 [SMILES: CSc1nc(Nc2cccc(C)c2)c2c(=O)[nH]ccc2n1]

A round bottom flask was charged with 4-[(3-methylphenyl)amino]-2-(methylthio)pyrido[4,3-d]pyrimidin-5(6H)-one (1.61 g, 5.58 mmole) and DMF (100 mL). A solution of lithiumhexamethyldisilazane in THF (1M, 33.4 mL) was added and the reaction was stirred at 125° C. overnight. Approximately 20 mL of THF was distilled away to get temperature up to 125° C. The reaction mixture was cooled in ice-water bath and quenched by dropwise addition of saturated aqueous solution of NH₄Cl. The mixture was concentrated under vacuum and the solid material was then partitioned between ethyl acetate and water. The phases were separated and the aqueous phase was extracted with ethyl acetate (2×). The organic extracts were combined and washed with water, brine and dried over MgSO₄. The solvent was removed under vacuum and the residue was subjected to column chromatography (silica gel, eluting with hexane/ethyl acetate gradient) to yield the crude product (1.2 g). It was then re-crystallized from ethyl acetate to give pure product (0.52 g, 30% yield).

MS: M(C₁₅H₁₄N₄O₁S₁)=298.37, (M+H)⁺=299.0.

¹H NMR (400 MHz, DMSO-d₆) δ ppm 2.33 (s, 3H), 2.54 (s, 3H), 6.33 (dd, J=7.2, 1.1 Hz, 1H) 6.96 (d, J=7.6 Hz, 1H), 7.28 (t, J=7.7 Hz, 1H), 7.55-7.66 (m, 3H), 11.92-11.97 (m, 1H), 11.99 (s, 1H).

Example 1

2-[(3-aminopropyl)amino]-4-[(3-methylphenyl)amino]pyrido[4,3-d]pyrimidin-5(6H)-one

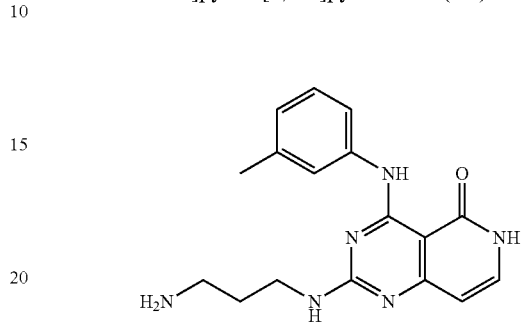

To a solution of 4-[(3-methylphenyl)amino]-2-(methylthio)pyrido[4,3-d]pyrimidin-5(6H)-one (0.52 g, 1.74 mmol) in DMF (30 mL) was added m-chloroperoxybenzoic acid (0.81 g, 70%-77% purity), and the reaction mixture was stirred overnight. 1,3-diamino propane (1.29 g, 17.4 mmol) was added and the reaction was stirred for 1 h and DMF was then removed under vacuum. The residue was dissolved in methanol and added to the top of SCX cartridge, (15 grams of silica-bond propylsulfonic acid), eluted with methanol until all of the chlorobenzoic acid came off. It was then eluted with 2N NH₃ in methanol to get off product. Fractions containing product were concentrated and purified using reverse-phase HPLC.

MS: M(C₁₇H₂₀N₆O)=324.39, (M+H)⁺=325.0.

1H NMR (400 MHz, DMSO-d₆) δ ppm 1.55-1.78 (m, 2H, 2.32 (s, 3H), 2.57-2.70 (m, 1H), 2.91-3.09 (m, 1H), 5.85-6.26 (m, 1H), 6.56-7.89 (m, 7H), 11.43-12.15 (m, 1H).

The following 2-[(3-aminopropyl)amino]-4-[(substituted)amino]pyrido[4,3-d]pyrimidin-5(6H)-one were prepared from ethyl 4-chloro-6-methyl-2-(methylthio)-5 pyrimidinecarboxylate and appropriate anilines following a synthetic route similar to that described for Example 1.

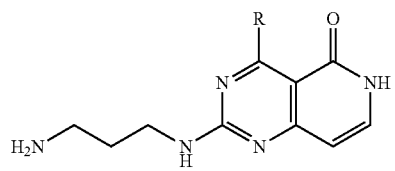

| Ex. No. | R | MS | (M + H)⁺ (m/z) | NMR |
|---|---|---|---|---|
| 2 | ![benzyl-NH-CH3] | C₁₇H₂₀N₆O₁ 324.39 | 325.2 | 1H NMR (400 MHz, DMSO-d₆) δ ppm 1.71-1.91 (m, 2 H), 2.77-2.95 (m, 2 H), 3.29-3.55 (m, 2 H), 4.80 (d, J = 5.8 Hz, 2 H), 6.18-6.38 (m, 1 H), 7.17-7.47 (m, 6 H), 7.58-7.97 (m, 1 H), 8.54-9.00 (m, 1 H), 10.24-10.87 (m, 1 H), 11.92-12.50 (m, 1 H) |

-continued

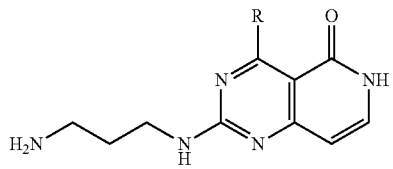

| Ex. No. | R | MS | (M + H)+ (m/z) | NMR |
|---|---|---|---|---|
| 3 | ![phenyl-NH-CH2] | C₁₆H₁₈N₆O₁ 310.36 | 311.0 | 1H NMR (400 MHz, DMSO-d₆) δ ppm 1.72-1.98 (m, 2 H), 2.73-2.94 (m, 2 H), 3.24-3.56 (m, 2 H), 6.06-6.42 (m, 1 H), 6.86-8.02 (m, 6 H), 11.53-12.51 (m, 2 H) |
| 4 | ![2-F-phenyl-NH-CH2] | C₁₆H₁₇F₁₂N₆O 328.35 | 329.0 | 1H NMR (400 MHz, DMSO-d₆) δ ppm 1.77-1.95 (m, 2 H), 2.76-2.98 (m, 2 H), 3.35-3.55 (m, 2 H), 6.09-6.38 (m, 1 H), 7.02-7.58 (m, 5 H), 8.38-8.92 (m, 2 H), 11.39-12.60 (m, 3 H) |

Example 5

2-[(3-aminopropyl)amino]-8-methyl-4-[(3-methylphenyl)amino]pyrido[4,3-d]pyrimidin-5(6H)-one

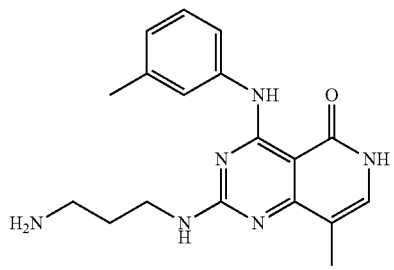 [SMILES: Cc1cccc(Nc2nc(NCCCN)nc3c(C)c[nH]c(=O)c23)c1]

This compound was prepared from diethyl propylidenepropanedioate following a synthetic route similar to that described for Example 1.

MS: M(C₁₈H₂₂N₆O)=338.41, (M+1)⁺=339.0
¹HNMR (400 mHz, DMSO-d₆) δ ppm 9.10 (1H, m), 7.87 (3H, m), 7.75 (1H, d, J=8.0 Hz), 7.61 (1H, s), 7.55 (1H, d, J=8.0 Hz), 7.34 (1H, m), 7.08 (1H, d, J=8.0 Hz), 3.55 (2H, m), 2.90 (2H, m), 2.36 (3H, s), 2.14 (3H, s), 1.94 (2H, m).

Intermediate 8

4-methyl-2-(methylthio)-6-{[4-(methylthio)phenyl]amino}-5-pyrimidinecarboxamide

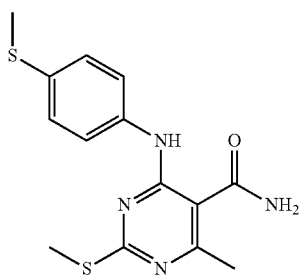 [SMILES: CSc1ccc(Nc2nc(SC)nc(C)c2C(N)=O)cc1]

The compound was prepared from ethyl 4-chloro-6-methyl-2-(methylthio)-5-pyrimidinecarboxylate and 4-(methylthio)aniline using a procedure similar to that as described for Intermediate 6.

MS: (C₁₄H₁₆N₄OS₂)=320.44, (M+H)⁺=320.8
1H NMR (400 MHz, DMSO-d₆) δ ppm 2.38 (s, 3H), 2.44 (s, 3H), 2.69 (s, 3H), 7.09-7.33 (m, 2H), 7.50-7.66 (m, 2H), 7.85 (br. s, 1H), 8.00 (br. s, 1H), 9.15 (br. s, 1H).

Intermediate 9

5-[(E)-2-(dimethylamino)ethenyl]-7-(methylthio)-1-[4-(methylthio)phenyl]-pyrimido[4,5-d]pyrimidin-4(1H)-one

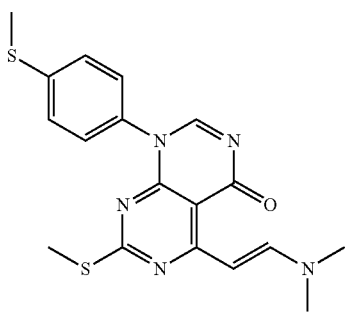 [SMILES: CSc1ccc(-n2cnc(=O)c3c(/C=C/N(C)C)nc(SC)nc32)cc1]

To a solution of 4-methyl-2-(methylthio)-6-{[4-(methylthio)phenyl]amino}-5-pyrimidinecarboxamide benzamide (0.50 g, 1.57 mmol) in DMF (20 ml) was added dimethylormamide-dimethylacetal (0.56 g, 4.7 mmol), and the reaction mixture was stirred at 85° for 1.5 h. It was cooled to room temperature and DMF was removed under vacuum. The residue was chromatographed (silica gel, eluting with hexane to ethyl acetate gradient followed by 10% methanol in methylene chloride) to yield the product (0.43 g, 72% yield).

MS: M(C₁₈H₁₉N₅O₁S₂)=385.51, (M+H)⁺=385.9.
1H NMR (400 MHz, DMSO-d₆) δ ppm 2.27 (s, 3H), 2.53 (s, 3H), 2.97 (s, 3H), 3.23 (s, 3 H), 7.04 (d, J=12.4 Hz, 1H), 7.39 (m, 2H), 7.46 (m, 2H), 8.28-8.38 (m, 2H).

Intermediate 10

2-(methylthio)-4-{[4-(methylthio)phenyl]amino}pyrido[4,3-d]pyrimidin-5(6H)-one

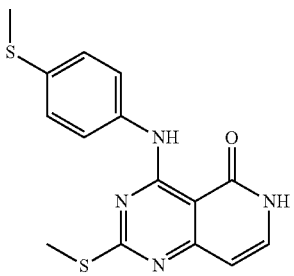 [SMILES: CSc1ccc(Nc2nc(SC)nc3cc[nH]c(=O)c23)cc1]

A round bottom flask was charged with 5-[(E)-2-(dimethylamino)ethenyl]-7-(methylthio)-1-[4-(methylthio)phenyl]pyrimido[4,5-d]pyrimidin-4(1H)-one (0.43 g, 1.30 mmol) and acetic acid (50 mL). The reaction was stirred at reflux for 18 h and acetic acid was removed under vacuum. Methylene chloride (20 mL) was added to the residue and the product was collected by filtration (0.27 g, 75% yield).

MS: $M(C_{15}H_{14}N_4O_1S_2)=330.43$, $(M+H)^+=330.8$.

$^1$H NMR (400 MHz, DMSO-$d_6$) δ ppm 2.48 (s, 3H), 2.52 (s, 3H), 5.99-6.47 (m, 1H), 7.04-7.41 (m, 2H), 7.54-7.64 (m, 1H), 7.69-7.79 (m, 2H), 11.62-12.13 (m, 1H).

Example 6

2-[(3-aminopropyl)amino]-4-{[4-(methylsulfonyl)phenyl]amino}pyrido[4,3-d]pyrimidin-5(6H)-one

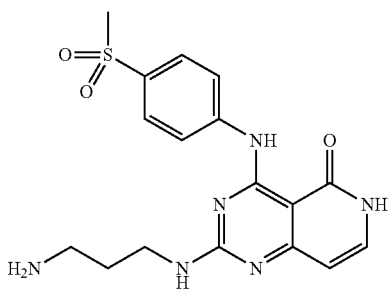 [SMILES: CS(=O)(=O)c1ccc(Nc2nc(NCCCN)nc3cc[nH]c(=O)c23)cc1]

To a solution of 2-(methylthio)-4-{[4-(methylthio)phenyl]amino}pyrido[4,3-d]pyrimidin-5(6H)-one (0.27 g, 0.817 mmol) in DMF (10 mL) was added meta-chloroperoxyoxybenzoic acid (0.77 g, 3.43 mmol)), and the reaction mixture was stirred at room temperature for 18 h. 1,3-diaminopropane (10 eq.) was added and the mixture was stirred for 2 h. DMF was removed under vacuum. The residue was dissolved in methanol and loaded to the top of SCX cartridge (15 grams of silica-bond propylsulfonic acid). It was eluted with methanol until all of the chlorobenzoic acid came off and then with 2N NH$_3$ in methanol to get off product. Fractions containing product were combined and concentrated. The residue was purified reverse-phase HPLC to give the product (0.34 g).

MS: $M(C_{17}H_{20}N_6O_3S)=388.45$, $(M+H)^+=389.1$.

$^1$H NMR (400 MHz, DMSO-$d_6$) δ ppm 1.75-1.97 (m, 2H), 2.82-2.97 (m, 2H), 3.22 (s, 3H), 3.35-3.53 (m, 2H), 6.15-6.31 (m, 1H), 7.40-7.62 (m, 1H), 7.63-7.77 (m, 3H), 7.82-8.16 (m, 4H), 11.57-11.94 (m, 1H), 12.29-12.59 (m, 1H).

Example 7

2-[(3-aminopropyl)amino]-4-{[3-(methylsulfonyl)phenyl]amino}pyrido[4,3-d]pyrimidin-5(6H)-one

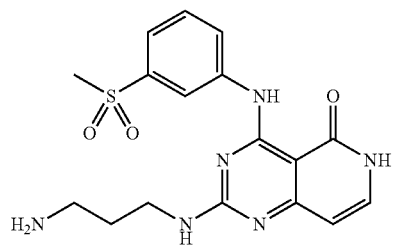 [SMILES: CS(=O)(=O)c1cccc(Nc2nc(NCCCN)nc3cc[nH]c(=O)c23)c1]

This compound was prepared from Intermediate 3 and 3-(methylthio)aniline using a synthetic route similar to that described for Example 6.

MS: $(C_{17}H_{20}N_6O_3S)=388.45$, $(M+1)^+=388.9$

1H NMR (400 MHz, DMSO-$d_6$) δ ppm 1.72-1.97 (m, 2H), 2.80-2.97 (m, 2H), 3.26 (s, 3 H), 3.37-3.59 (m, 2H), 6.17-6.33 (m, 1H), 7.58-7.86 (m, 7H), 8.86-8.97 (m, 1H), 11.48-12.14 (m, 1H), 12.37-12.63 (m, 1H).

Intermediate 11

Ethyl 4-({3-[3-({[(1,1-dimethylethyl)oxy]carbonyl}amino)propyl]phenyl}amino)-6-methyl-2-(methylthio)-5-pyrimidinecarboxylate

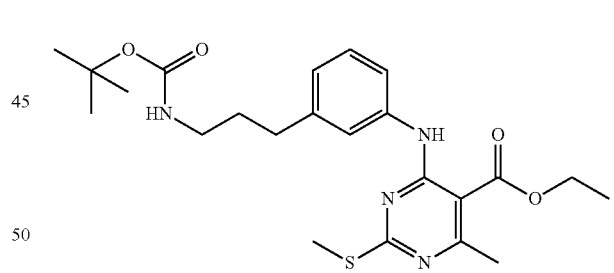

To a solution of 1,1-dimethylethyl[3-(3-aminophenyl)propyl]carbamate (390 mg, 1.558 mmol) in DMF (5 mL) were added ethyl 4-chloro-6-methyl-2-(methylthio)-5-pyrimidinecarboxylate (307 mg, 1.246 mmol) and DIEA (0.298 mL, 1.714 mmol), and the reaction mixture was stirred at 75° C. overnight. The reaction was then concentrated and the residue was purified using column chromatography (silica gel, 0% to 50% EtOAc gradient in hexane) to afford the product (210 mg, 29% yield).

MS: $M(C_{23}H_{32}N_4O_4S)=460.59$, $(M+H)^+=461.6$

1H NMR (400 MHz, CD$_3$OD) δ ppm 1.44-1.47 (m, 12H), 1.77-1.85 (m, 3H), 2.52 (s, 3 H), 2.62 (s, 3H), 2.65 (d, J=8.6 Hz, 2H), 3.09 (t, J=7.0 Hz, 2H), 4.45 (q, J=7.2 Hz, 2 H), 4.64

(br. s., 1H), 7.01 (d, J=7.6 Hz, 1H), 7.28 (t, J=7.8 Hz, 1H), 7.42 (d, J=1.3 Hz, 1H), 7.55-7.58 (m, 1H).

Intermediate 12

1,1-dimethylethyl[3-(3-{[5-(aminocarbonyl)-6-methyl-2-(methylthio)-4-pyrimidinyl]amino}phenyl)propyl]carbamate

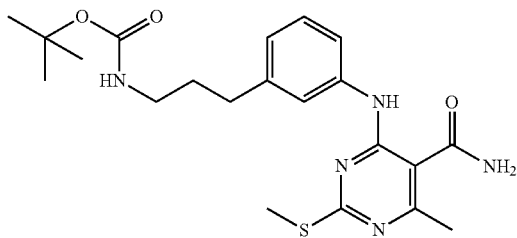 [SMILES: CSc1nc(C)c(C(N)=O)c(Nc2cccc(CCCNC(=O)OC(C)(C)C)c2)n1]

This compound was prepared from ethyl 4-({3-[3-({[(1,1-dimethylethyl)oxy]carbonyl}amino)propyl]phenyl}amino)-6-methyl-2-(methylthio)-5-pyrimidinecarboxylate using a synthetic route similar to that described for Intermediate 6.

MS: M($C_{21}H_{29}N_5O_3S$)=431.55, (M+H)$^+$=432.0

1H NMR (400 MHz, CDCl$_3$) δ ppm 1.40 (s, 9H), 1.78 (quin, J=7.4 Hz, 2H), 2.49 (s, 3H), 2.51 (s, 3H), 2.61 (d, J=7.6 Hz, 2H), 3.06-3.13 (m, 2H), 3.36 (dt, J=3.3, 1.6 Hz, 1H), 6.93 (d, J=7.6 Hz, 1H), 7.22 (t, J=7.8 Hz, 1H), 7.41 (d, J=7.8 Hz, 2H), 9.47-9.50 (m, 1H).

Intermediate 13

1,1-dimethylethyl[3-(3-{[2-(methylthio)-5-oxo-5,6-dihydropyrido[4,3-d]pyrimidin-4-yl]amino}phenyl)propyl]carbamate

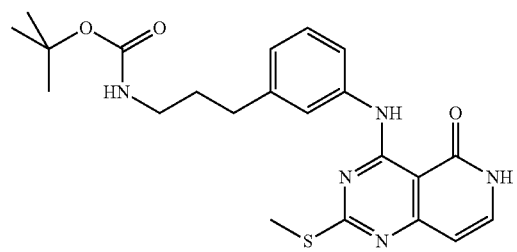 [SMILES: CSc1nc(Nc2cccc(CCCNC(=O)OC(C)(C)C)c2)c2c(=O)[nH]ccc2n1]

1,1-Dimethylethyl[3-(3-{[5-(aminocarbonyl)-6-methyl-2-(methylthio)-4-pyrimidinyl]amino}phenyl)propyl]carbamate (100 mg, 0.232 mmol) was dissolved into DMF (2 mL) and DMF-DMA (0.093 mL, 0.695 mmol) added. The solution was stirred at 80° C. for 2 h. The solvent was removed and acetic acid (1 mL) was added and the mixture was heat at 90° C. with stirring overnight. The reaction was then concentrated under reduced pressure and was purified using reverse-phase HPLC (Gilson using Trilution software with a phenomenex Luna 5u C18(2) 100A, AXIA. 50×30.00 mm 5 micron. 7.3-minute run, 47 ml/min: 35% ACN/H$_2$O, 0.1% TFA to 65% ACN/H$_2$O, 0.1% TFA with UV detection at 254 nm) to afford the product (10 mg).

MS: M($C_{22}H_{27}N_5O_3S$)=441.55 (M+H)$^+$=442.1

1H NMR (400 MHz, CD$_3$OD) δ ppm 1.46 (s, 9H), 1.83 (d, J=7.6 Hz, 2H), 2.03 (d, J=7.8 Hz, 1H), 2.69 (s, 3H), 2.79 (t, J=7.8 Hz, 1H), 2.98 (d, J=7.6 Hz, 1H) 3.09 (t, J=6.9 Hz, 2H), 6.40-6.44 (m, 1H), 7.16 (d, J=7.8 Hz, 1H), 7.38 (t, J=7.7 Hz, 2H), 7.56 (s, 1H), 7.63-7.74 (m, 2H), 7.76 (d, J=7.3 Hz, 1H).

Intermediate 14

1,1-dimethylethyl(3-{3-[(2-{[3-({[(1,1-dimethylethyl)oxy]carbonyl}amino)propyl]amino}-5-oxo-5,6-dihydropyrido[4,3-d]pyrimidin-4-yl)amino]phenyl}propyl)carbamate

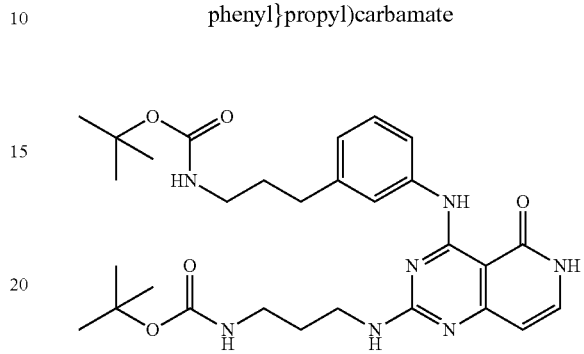

1,1-Dimethylethyl[3-(3-{[2-(methylthio)-5-oxo-5,6-dihydropyrido[4,3-d]pyrimidin-4-yl]amino}phenyl)propyl]carbamate (19 mg, 0.043 mmol) was dissolved into DMF (1 mL) and m-CPBA (27.3 mg, 0.108 mmol) was added. The reaction mixture was stirred for 2 h and 1,1-dimethylethyl(3-aminopropyl)carbamate (60.0 mg, 0.344 mmol) was added. The reaction mixture was stirred overnight. It was then concentrated and the residue was purified using reverse-phase HPLC (Gilson using Trilution software with a phenomenex Luna 5u C18(2) 100A, AXIA. 50×30.00 mm 5 micron. 7.3-minute run, 47 ml/min: 25% ACN/H$_2$O, 0.1% TFA to 65% ACN/H$_2$O, 0.1% TFA with UV detection at 254 nm) to afford the product (39 mg).

MS: M($C_{29}H_{41}N_7O_5$)=567.68, (M+H)$^+$=568.5

1H NMR (400 MHz, CDCl$_3$) δ ppm 1.40-1.56 (m, 18H), 1.85 (br. s, 2H), 2.28 (br. s, 4H), 2.67 (br. s., 2H), 3.17 (d, J=6.8 Hz, 3H), 3.60 (m, 2H), 5.10 (m, 1H), 6.24 (m, 1H), 6.54 (m, 1H), 6.78-6.94 (m, 1H), 7.02 (s, 1H), 7.44 (m, 1H), 7.61 (m, 1H), 9.96 (d, J=6.3 Hz, 1H), 10.80 (br. s., 1H), 12.06 (br. s., 1H).

Example 8

2-[(3-aminopropyl)amino]-4-{[3-(3-aminopropyl)phenyl]amino}pyrido[4,3-d]pyrimidin-5(6H)-one

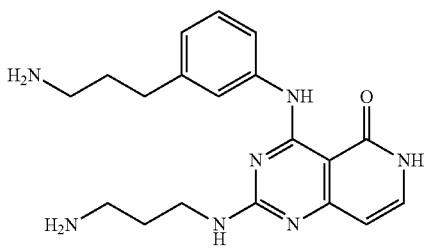 [SMILES: NCCCNc1nc(Nc2cccc(CCCN)c2)c2c(=O)[nH]ccc2n1]

To a premixed solution of TFA (0.5 mL, 6.49 mmol) and dichloromethane (0.5 mL) was added to 1,1-dimethylethyl(3-{3-[(2-{[3-({[(1,1-dimethylethyl)oxy]carbonyl}amino)propyl]amino}-5-oxo-5,6-dihydropyrido[4,3-d]pyrimidin-4-yl)amino]phenyl}propyl)carbamate (39 mg, 0.069 mmol) and the mixture was stirred for 30 min. It was then concentrated and the product was lyophilized (30 mg, white solid).

MS: M($C_{19}H_{25}N_7O$)=367.45 (M+H)$^+$=368.0

1H NMR (400 MHz, DMSO-d$_6$) δ ppm 1.80-1.93 (m, 4H), 2.65-2.70 (m, 2H), 2.76-2.88 (m, 4H), 3.50 (br. s, 4H), 6.33 (br. s, 1H), 6.97 (br. s, 1H), 7.07 (d, J=7.6 Hz, 1H), 7.29-7.36 (m, 1H), 7.39 (t, J=7.8 Hz, 1H), 7.47 (s, 1H), 7.83 (d, J=7.6 Hz, 1H), 7.95 (s, 1H), 8.02-8.07 (m, 1H), 12.04 (br. s, 1H), 12.35 (br. s, 1H).

Intermediate 15 ethyl 4-({3-[2-(1,3-dioxo-1,3-dihydro-2H-isoindol-2-yl)ethyl]phenyl}amino)-6-methyl-2-(methylthio)-5-pyrimidinecarboxylate

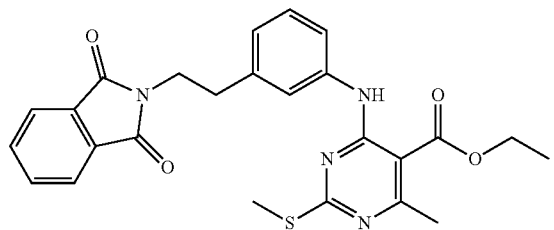 [SMILES: CCOC(=O)c1c(C)nc(SC)nc1Nc1cccc(CCN2C(=O)c3ccccc3C2=O)c1]

The compound was prepared from 2-[2-(3-aminophenyl)ethyl]-1H-isoindole-1,3(2H)-dione and ethyl 4-chloro-6-methyl-2-(methylthio)-5-pyrimidinecarboxylate following a synthetic route similar to that described for intermediate 11.

MS: M($C_{25}H_{24}N_4O_4S$)=476.55, (M+H)$^+$=476.8

1H NMR (400 MHz, CDCl$_3$) δ ppm 1.42 (t, J=7.4 Hz, 3H), 2.57 (s, 3H), 2.97-3.02 (m, 2 H), 3.11 (dd, J=7.3, 4.8 Hz, 2H), 3.93 (dd, J=9.7, 6.2 Hz, 2H), 4.44 (q, J=7.2 Hz, 2H), 7.08 (d, J=7.6 Hz, 1H), 7.28-7.32 (m, 1H), 7.45 (d, J=8.3 Hz, 1H), 7.63 (s, 1H), 7.72 (d, J=8.3 Hz, 2H), 7.84 (dd, J=5.6, 3.0 Hz, 2H), 10.80 (br. s., 1H).

Intermediate 16

4-({3-[2-(1,3-dioxo-1,3-dihydro-2H-isoindol-2-yl)ethyl]phenyl}amino)-6-methyl-2-(methylthio)-5-pyrimidinecarboxamide

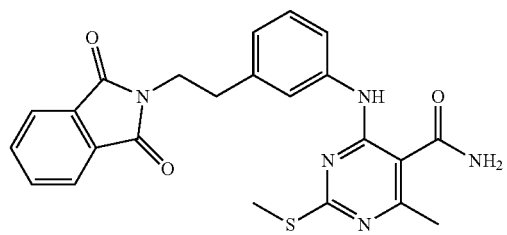 [SMILES: CSc1nc(C)c(C(N)=O)c(Nc2cccc(CCN3C(=O)c4ccccc4C3=O)c2)n1]

This compound was prepared from ethyl 4-({3-[2-(1,3-dioxo-1,3-dihydro-2H-isoindol-2-yl)ethyl]phenyl}amino)-6-methyl-2-(methylthio)-5-pyrimidinecarboxylate using a synthetic route similar to that described for intermediate 6.

MS: M($C_{23}H_{21}N_6O_3$)=447.51 (M+H)$^+$=448.1

1H NMR (400 MHz, DMSO-d$_6$) δ ppm 2.39 (s, 3H), 2.48 (s, 3H), 2.90 (t, J=7.6 Hz, 2H), 3.80 (d, J=7.8 Hz, 2H), 6.90 (d, J=7.6 Hz, 1H), 7.22 (t, J=7.8 Hz, 1H), 7.43 (d, J=1.5 Hz, 1H), 7.62 (s, 1H), 7.80-7.88 (m, 5H), 8.00 (s, 1H), 9.22 (s, 1H).

Intermediate 17

2-[2-(3-{[2-(Methylthio)-5-oxo-5,6-dihydropyrido[4,3-d]pyrimidin-4-yl]amino}phenyl)ethyl]-1H-isoindole-1,3(2H)-dione

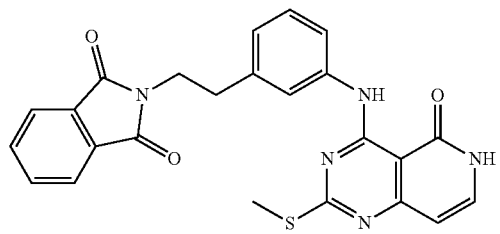 [SMILES: CSc1nc(Nc2cccc(CCN3C(=O)c4ccccc4C3=O)c2)c2c(=O)[nH]ccc2n1]

N-[2-(3-{[5-(aminocarbonyl)-6-methyl-2-(methylthio)-4-pyrimidinyl]amino}phenyl)ethyl]-1,2-benzenedicarboxamide (100 mg, 0.215 mmol) was dissolved in DMF (1 mL) and DMF-DMA (0.144 mL, 1.076 mmol) was added. The solution was stirred at 80° C. for 2 h. The solvent was then removed and acetic acid (1 mL) was added and the mixture was stirred at 90° C. overnight. The reaction mixture was concentrated under reduced pressure and the residue was purified using reverse-phase HPLC (Gilson using Trilution software with a phenomenex Luna 5u C18(2) 100A, AXIA. 50×30.00 mm 5 micron. 7.3-minute run, 47 ml/min: 28% ACN/H$_2$O, 0.1% TFA to 50% ACN/H$_2$O, 0.1% TFA with UV detection at 254 nm) to afford the product (38 mg).

MS: M($C_{24}H_{16}N_6O_3S$)=457.50, (M+H)$^+$=458.1

1H NMR (400 MHz, DMSO-d$_6$) δ ppm 2.56 (s, 3H), 2.95 (t, J=7.3 Hz, 2H), 3.84 (t, J=7.3 Hz, 2H), 6.34 (dd, J=7.2, 1.14 Hz, 1H), 6.97 (d, J=7.8 Hz, 1H), 7.29 (t, J=7.8 Hz, 1H), 7.59 (t, J=6.7 Hz, 2H), 7.75 (s, 1H), 7.83 (m, 4H), 11.96 (d, J=6.1 Hz, 1H), 12.01 (s, 1H).

Intermediate 18

1,1-dimethylethyl(3-{[4-({3-[2-(1,3-dioxo-1,3-dihydro-2H-isoindol-2-yl)ethyl]phenyl}amino)-5-oxo-5,6-dihydropyrido[4,3-d]pyrimidin-2-yl]amino}propyl)carbamate

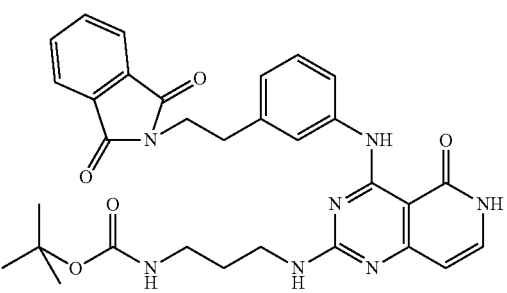 [SMILES: CC(C)(C)OC(=O)NCCCNc1nc(Nc2cccc(CCN3C(=O)c4ccccc4C3=O)c2)c2c(=O)[nH]ccc2n1]

2-[2-(3-{[2-(Methylthio)-5-oxo-5,6-dihydropyrido[4,3-d]pyrimidin-4-yl]amino}phenyl)ethyl]-1H-isoindole-1,3(2H)-dione (38 mg, 0.083 mmol) was dissolved in DMF (1 mL) and m-CPBA (52.7 mg, 0.208 mmol) was added. The reaction mixture was stirred overnight and 1,1-dimethylethyl (3-aminopropyl)carbamate (116 mg, 0.664 mmol) was added. The mixture was stirred for 1 h and concentrated. The residue was purified using reverse-phase HPLC (Gilson using Trilution software with a phenomenex Luna 5u C18(2) 100A, AXIA. 50×30.00 mm 5 micron. 7.3-minute run, 47 ml/min: 30% ACN/H$_2$O, 0.1% TFA to 55% ACN/H$_2$O, 0.1% TFA with UV detection at 254 nm) to afford the product (24 mg).

MS: M(C$_{31}$H$_{33}$N$_7$O$_5$)=583.64, (M+H)$^+$=584.1

1H NMR (400 MHz, DMSO-d$_6$) δ ppm 1.32 (s, 9H), 1.73 (br. s., 2H), 2.97 (s, 4H), 3.44 (br. s., 2H), 3.57 (br. s., 2H), 3.85 (br. s., 2H), 6.35 (m, 1H), 6.86 (m, 1H), 7.04 (m, 1 H), 7.34 (t, 1H), 7.46 (s, 1H), 7.61 (d, 1H), 7.72-7.75 (m, 1H), 7.84 (m, 4H), 12.37 (s, 1 H).

Intermediate 19

1, 1-Dimethylethyl{3-[(4-{[3-(2-aminoethyl)phenyl] amino}-5-oxo-5,6-dihydropyrido[4,3-d]pyrimidin-2-yl)amino]propyl}carbamate

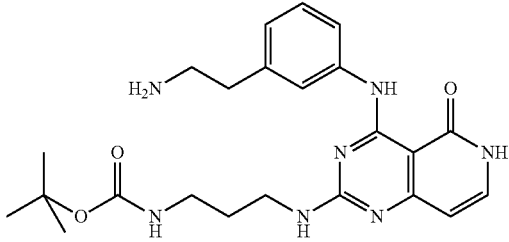 [SMILES: CC(C)(C)OC(=O)NCCCNc1nc(Nc2cccc(CCN)c2)c2c(=O)[nH]ccc2n1]

1,1-Dimethylethyl(3-{[4-({3-[2-(1,3-dioxo-1,3-dihydro-2H-isoindol-2-yl)ethyl]phenyl}amino)-5-oxo-5,6-dihydropyrido[4,3-d]pyrimidin-2-yl]amino}propyl)carbamate (24 mg, 0.041 mmol) was dissolved in ethanol (2 mL) and hydrazine (30 µl, 0.956 mmol) was added. The reaction was stirred at 90° C. for 3 h. The reaction mixture was concentrated and the residue was purified using reverse-phase HPLC (Gilson using Trilution software with a phenomenex Luna 5u C18(2) 100A, AXIA. 50×30.00 mm 5 micron. 7.3-minute run, 47 ml/min: 10% ACN/H$_2$O, 0.1% TFA to 40% ACN/H$_2$O, 0.1% TFA with UV detection at 254 nm) to afford the product (11 mg).

MS: M(C$_{23}$H$_{31}$N$_7$O$_3$)=453.54, (M+1)$^+$=454.0

Example 9

4-{[3-(2-aminoethyl)phenyl]amino}-2-[(3-aminopropyl)amino]pyrido[4,3-d]pyrimidin-5(6H)-one

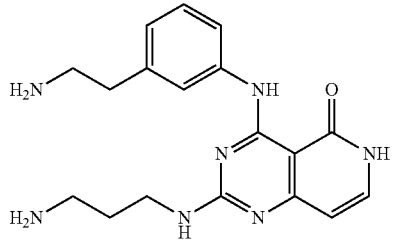 [SMILES: NCCCNc1nc(Nc2cccc(CCN)c2)c2c(=O)[nH]ccc2n1]

To a premixed solution of TFA (0.5 mL, 6.49 mmol) and dichloromethane (0.5 mL) was added to 1,1-dimethyl-ethyl{3-[(4-{[3-(2-aminoethyl)phenyl]amino}-5-oxo-5,6-dihydropyrido[4,3-d]pyrimidin-2-yl)amino]propyl}carbamate (11 mg, 0.024 mmol) and the reaction mixture was stirred for 30 min. It was concentrated and the product lypholized (4 mg, white solid).

MS: M(C$_{18}$H$_{23}$N$_7$O)=353.43, (M+H)$^+$=354.2

1H NMR (400 MHz, DMSO-d$_6$) δ ppm 1.84-1.95 (m, 2H), 2.83-2.95 (m, 4H), 3.02-3.16 (m, 2H), 3.40-3.55 (m, 2H), 6.39 (d, J=6.8 Hz, 1H), 7.16 (d, J=8.1 Hz, 1H), 7.45 (t, J=8.0 Hz, 2H), 7.74-7.92 (m, 6H), 9.03 (br. s., 1H), 12.43 (s, 1H), 12.49 (br. s, 1H).

Example 10

4-{[4-(2-aminoethyl)phenyl]amino}-2-[(3-aminopropyl)amino]pyrido[4,3-d]pyrimidin-5(6H)-one

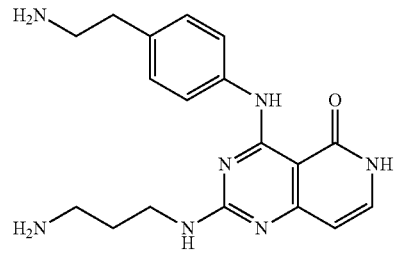 [SMILES: NCCCNc1nc(Nc2ccc(CCN)cc2)c2c(=O)[nH]ccc2n1]

The compound was prepared from Intermediate 3 and 2-[2-(4-aminophenyl)ethyl]-1H-isoindole-1,3(2H)-dione following the procedure as a synthetic route similar to that described for Example 9.

MS: M(C$_{18}$H$_{23}$N$_7$O)=353.43, (M+1)$^+$=354.1

1H NMR (400 MHz, DMSO-d$_6$) δ ppm 2.88 (d, J=8.6 Hz, 4H), 2.98-3.12 (m, 2H), 3.36-3.57 (m, 2H), 6.19-6.39 (m, 1H), 7.34 (s, 2H), 7.64-8.10 (m, 8H), 11.49-12.51 (m, 2H).

Example 11

2-[(3-aminopropyl)amino]-8-methyl-4-[(3-methylphenyl)amino]pyrido[4,3-d]pyrimidin-5(6H)-one

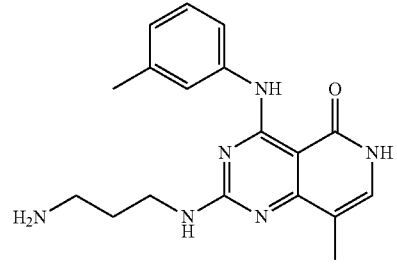

This compound was prepared from diethyl propylidenepropanedioate following a synthetic route similar to that described for Example 1.

MS: M(C$_{18}$H$_{22}$N$_6$O)=338.41, (M+1)$^+$=339.0

¹HNMR (400 mHz, DMSO-d₆) δ ppm 9.10 (1H, m), 7.87 (3H, m), 7.75 (1H, d, J=8.0 Hz), 7.61 (1H, s), 7.55 (1H, d, J=8.0 Hz), 7.34 (1H, m), 7.08 (1H, d, J=8.0 Hz), 3.55 (2H, m), 2.90 (2H, m), 2.36 (3H, s), 2.14 (3H, s), 1.94 (2H, m).

Intermediate 20

[1-(methyloxy)ethylidene]propanedinitrile

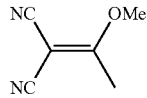

To a 100 mL flask equipped with air stirrer and thermometer and distillation condensor were added malononitrile (9.1 g, 0.138 mol), triethyl orthoacetate (26.8 g, 0.165 mol) and glacial acidic acid (0.4 mL) sequentially, and the mixture was stirred and gently heated (90° C.) until the ethanol formed in the reaction began to distill off. When all the ethanol had distilled off, the reaction temperature was raised slowly from 90° C. to 140° C. for 30 min to ensure completion of the reaction. The reaction mixture was allowed to cool to 45° C. to solidify. The resulting solid mass was broken up under hexane (20 mL) and hexane was decanted off. The solid was washed with ethanol (50 mL) to afford a colorless crystal. The ethanol solution was concentrated and allowed to cool to room temperature. Then the crystal was filtered, washed with ethanol dried under vacuum (12.3 g, 65.9% yield).

¹H NMR (300 MHz, DMSO), 64.42 (2H, q, J=15.8, 6.8 Hz), 2.44 (3H, s), 1.32 (3H, t, J=6.9 Hz).

Intermediate 21

4-amino-6-methyl-2-(methylthio)-5-pyrimidinecarbonitrile

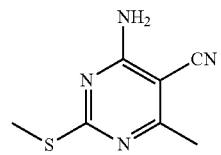

To a mixture of (1-ethoxylethylidene)malononitrile (25 g, 0.184 mol) and s-methlyisothiourea hemisulfate salt (38.3 g, 0.275 mol) in MeOH (800 mL) was added NaOMe (9.9 g, 0.184 mol) at 0° C. The mixture was warmed up to RT and stirred overnight. Water (1 L) was added to the reaction mixture and it was stirred for additional 30 min. The resulting precipitate was filtered and washed with water until the eluting water turned colorless. The white (or yellow) solid was dried under vacuum (26.1 g, 78.8% yield).

MS: M(C₇H₈N₄S)=180.23, (M+1)⁺=181.1

¹H NMR (300 MHz, DMSO), δ 7.75 (2H, br.s), 2.43 (3H, s), 2.36 (3H, s).

Intermediate 22

4-chloro-6-methyl-2-(methylthio)-5-pyrimidinecarbonitrile

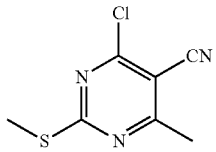

4-amino-6-methyl-2-(methylthio)pyrimidine-5-carbonitrile (50 g, 0.278 mol) was added to a mixture of anhydrous copper (II) chloride (44.7 g, 0.334 mol), tert-butylnitrite (51.6 mL, 0.500 mol) and MgSO₄ (10 mg) in acetonitrile (800 mL) at 80° C. with stirring. After 3 h, the mixture was cooled to RT and filtered. The filtrate was concentrated and the residue was dissolved in ethyl acetate, washed with water, brine, dried over MgSO₄ and concentrated. Column chromatography of the crude material (PE/EtOAc=3:1, then 3:2) afforded the desired product as a white solid (33 g, 59% yield).

MS: M(C₇H₆N₃SCI)=199.66, (M+1)⁺=200.1

¹H NMR (300 MHz, DMSO) δ 2.69 (3H, s), 2.61 (3H, s).

Intermediate 23

4-methyl-6-[(3-methylphenyl)amino]-2-(methylthio)-5-pyrimidinecarbonitrile

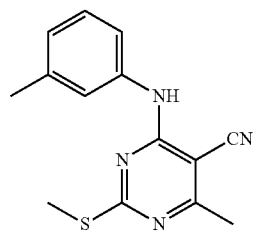 [SMILES: CSc1nc(C)c(C#N)c(Nc2cccc(C)c2)n1]

To a solution of 4-chloro-6-methyl-2-(methylthio)-5-pyrimidinecarbonitrile (500 mg, 2.51 mmol) in DMF (6 mL) were added 3-methylaniline (322 mg, 3.01 mmol) and diisopropyl ethylamine (712 mg, 5.52 mmol), and the reaction mixture was stirred 70° C. for 1.5 h. The mixture was cooled and concentrated, and the residue was dissolved into EtOAc (30 mL) and washed with water (10 mL). The ethyl acetate extract was dried over Na₂SO₄, filtered, and concentrated. The residue was purified using column chromatography (silica gel, hexane/EtOAc, 0 to 100%) to give the product (650 mg, 96% yield).

MS: M(C₁₄H₁₄N₄S)=270.36, (M+1)⁺=270.8

¹HNMR (400 mHz, DMSO-d₆) δ ppm 7.43 (1H, m), 7.27 (1H, m), 7.10 (1H, s), 7.01 (1H, d, J=8.0 Hz), 2.55 (3H, s), 2.52 (3H, s), 2.38 (3H, s).

Intermediate 24

4-[(E)-2-(dimethylamino)ethenyl]-6-[(3-methylphenyl)amino]-2-(methylthio)-5-pyrimidinecarbonitrile

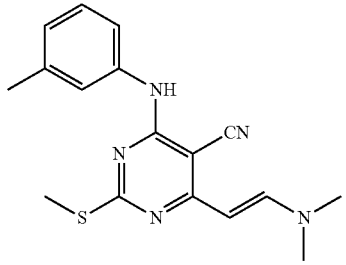

To a solution of 4-methyl-6-[(3-methylphenyl)amino]-2-(methylthio)-5-pyrimidinecarbonitrile (1.32 g, 4.89 mmol) in DMF (8 mL) was added DMF dimethyl acetyl (1.16 g, 9.75 mmol), and the reaction mixture was stirred at 110° C. for 1.5 h. The mixture was concentrated and the residue was dissolved into EtOAc (30 mL). The solution was washed with water and organic layer was collected. The aqueous layer was extracted with EtOAc (2×). The combined extract was dried over $Na_2SO_4$, filtered, and concentrated to give the crude enamine product (1.47 g). MS: $M(C_{17}H_{19}N_5S)$=325.44, $(M+1)^+$=326.1

Intermediate 25

5-bromo-N-(3-methylphenyl)-2-(methylthio)pyrido[4,3-d]pyrimidin-4-amine

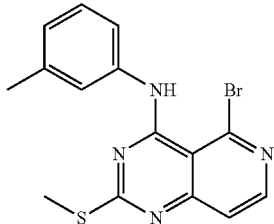 [SMILES: CSc1nc(Nc2cccc(C)c2)c2c(Br)nccc2n1]

The crude 4-[(E)-2-(dimethylamino)ethenyl]-6-[(3-methylphenyl)amino]-2-(methylthio)-5-pyrimidinecarbonitrile (1.47 g) was dissolved into acetic acid (5 mL) and a solution of 33% HBr in glacial acetic acid (10 mL) was added. The reaction mixture was stirred at room temperature for 20 min. The mixture was then concentrated under reduced pressure to give the bromopyridine as a HBr salt.

MS: $M(C_{15}H_{13}BrN_4S)$=361.27, $(M+1)^+$=360.7, 362.7

$^1$HNMR (400 mHz, DMSO-$d_6$) δ ppm 8.31 (1H, d, J=4 Hz), 7.55 (1H, m), 7.42 (2H, m), 7.31 (1H, m), 7.05 (1H, d, J=4 Hz), 2.56 (3H, s), 2.41 (3H, s).

Intermediate 26

4-[(3-methylphenyl)amino]-2-(methylthio)pyrido[4,3-d]pyrimidin-5(6H)-one

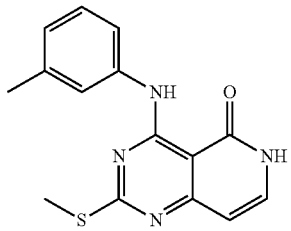 [SMILES: CSc1nc(Nc2cccc(C)c2)c2c(=O)[nH]ccc2n1]

The crude intermediate 25 was dissolved into acetic acid (10 mL) and aqueous 6N HCl solution (15 mL), and the reaction mixture was stirred at 80° C. for 1.5 h. The mixture was cooled and concentrated under reduced pressure. The residue was treated slowly with saturated $NaHCO_3$ and the solid was collected by filtration. The aqueous solution and extracted with $CH_2Cl_2$ (5×), dried over $Na_2SO_4$, filtered, and concentrated. The combined solid product was further dried under high vacuum to give the crude product (1.48 g, 84% pure).

MS: $M(C_{15}H_{14}N_4OS)$=298.37, $(M+1)^+$=298.9

$^1$HNMR (400 mHz, DMSO-d6) δ ppm 7.60 (3H, m), 7.28 (1H, t, J=8.0 Hz), 6.96 (1H, d, J=8.0 Hz), 6.34 (1H, d, J=8.0 Hz), 2.54 (3H, s), 2.33 (3H, s).

Intermediate 27

1,1-dimethylethyl[3-({4-[(3-methylphenyl)amino]-5-oxo-5,6-dihydropyrido[4,3-d]pyrimidin-2-yl}amino)propyl]carbamate

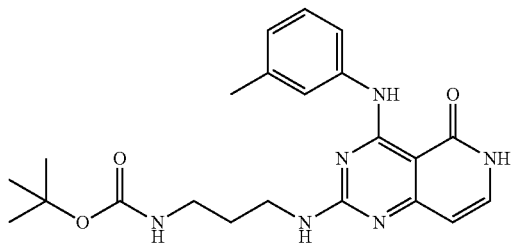 [SMILES: Cc1cccc(Nc2nc(NCCCNC(=O)OC(C)(C)C)nc3cc[nH]c(=O)c23)c1]

To a solution of 4-[(3-methylphenyl)amino]-2-(methylthio)pyrido[4,3-d]pyrimidin-5(6H)-one (420 mg, 1.41 mmol) in DMF (6 mL) was added mCPBA (582 mg, 3.38), and the reaction mixture was stirred overnight. 1,1-dimethylethyl (3-aminopropyl)carbamate (1.00 g, 8.06 mmol) was added and the mixture was stirred for 1 h. The reaction was quenched with saturated $NaHCO_3$ and extracted with ethyl acetate (3×15 mL). The extract was dried over $MgSO_4$, filtered, and concentrated. The residue was purified using reverse-phase HPLC to afford the product (301 mg).

HPLC conditions: Gilson using Trilution software, with a phenomenex Luna 5u C18(2) 100A, AXIA, 50×30.00 mm 5 micron, 7.3-minute run (47 mL/min, 23% $ACN/H_2O$, 0.1% TFA to 53% $ACN/H_2O$, 0.1% TFA) with UV detection at 254 nm.

MS: $M(C_{22}H_{28}N_6O_3)$=424.50, $(M+1)^+$=425.1

$^1$HNMR (400 mHz, DMSO-$d_6$) δ ppm 7.88 (1H, s), 7.72 (1H, d, J=8.0 Hz), 7.62 (1H, m), 7.41 (1H, d, J=8.0 Hz), 6.35 (1H, d, J=8.0 Hz), 4.54 (2H, s), 4.48 (2H, s), 2.53 (3H, s).

Example 1

2-[(3-aminopropyl)amino]-4-[(3-methylphenyl)amino]pyrido[4,3-d]pyrimidin-5(6H)-one

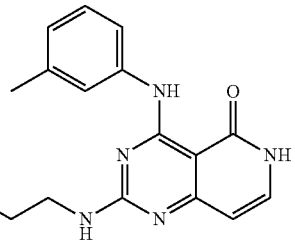

1,1-dimethylethyl[3-({4-[(3-methylphenyl)amino]-5-oxo-5,6-dihydropyrido[4,3-d]pyrimidin-2-yl}amino)propyl]carbamate (245 mg, 0.577 mmol) was dissolved into dichloromethane (3 mL) and TFA (1 mL) was added. The reaction mixture was stirred for 1 h and concentrated. The residue was further dried under high vacuum to afford the product as a TFA salt (250 mg).

Intermediate 28

1-(phenylsulfonyl)-1H-pyrazol-4-amine

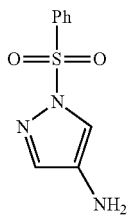

To a solution of 4-nitro-1-(phenylsulfonyl)-1H-pyrazole (21.0 g, 82.9 mmol) in methanol (300 mL) was added Pd/C (10% wt, 4.0 g), and the mixture was stirred for 12 h at room temperature under a $H_2$ atmosphere. After filtration, the filtrate was concentrated under reduced pressure. The resulting residue was washed with petroleum ether and dried to afford the product as a white solid (15.0 g, 81.1% yield).

MS: $M(C_9H_9N_3O_2S)$=223.26, $(M+1)^+$=224.0

Intermediate 29

4-methyl-2-(methylthio)-6-{[1-(phenylsulfonyl)-1H-pyrazol-4-yl]amino}-5-pyrimidinecarbonitrile

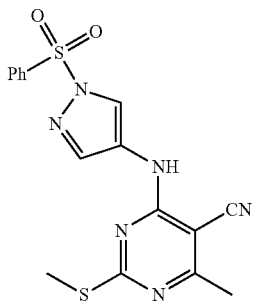 [SMILES: CSc1nc(C)c(C#N)c(Nc2cnn(S(=O)(=O)c3ccccc3)c2)n1]

Intermediate 30

4-methyl-2-(methylthio)-6-(1H-pyrazol-4-ylamino)-5-pyrimidinecarbonitrile

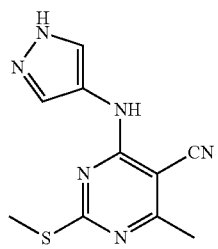 [SMILES: CSc1nc(C)c(C#N)c(Nc2cn[nH]c2)n1]

To a solution of 4-chloro-6-methyl-2-(methylthio)pyrimidine-5-carbonitrile (6.45 g, 32.2 mmol) and 1-(phenylsulfonyl)-1H-pyrazol-4-amine (7.2 g, 32.2 mmol) in 1,4-dioxane (150 mL) was added 4-methylbenzenesulfonic acid (3.06 g, 16.1 mmol). The reaction mixture was stirred overnight at 90° C. After cooling to room temperature, the precipitate was filtered, washed with saturated $NaHCO_3$ solution and then water, dried and washed with petroleum and the mixture solvent (petroleum ether:ethyl acetate=4:1) successively to give 4-methyl-2-(methylthio)-6-(1H-pyrazol-4-ylamino)-5-pyrimidinecarbonitrile (intermediate 30, 3.6 g) as a pale solid. MS: $M(C_{10}H_{10}N_6S)$=246.30, $(M+1)^+$=247.1; $^1$HNMR (300 mHz, DMSO-$d_6$) δ ppm 12.69 (1H, s), 9.87 (1H, s), 7.97 (1H, s), 3.33 (3H, m), 2.42 (3H, s). The organic eluents were concentrated under reduced pressure and the residue was treated with the same method above to afford 4-methyl-2-(methylthio)-6-{[1-(phenylsulfonyl)-1H-pyrazol-4-yl]amino}-5-pyrimidinecarbonitrile (intermediate 29, 4.26 g, 34.4% yield) as a yellow solid.

MS: $M(C_{16}H_{14}N_6O_2S_2)$=386.46, $(M+1)^+$=387.1; $^1$HNMR (300 mHz, DMSO-$d_6$) δ ppm 10.22 (1H, s), 8.68 (1H, s), 8.14 (1H, s), 7.96 (2H, d, J=7.5 Hz), 7.80 (1H, m), 7.68 (2H, m), 2.50 (3H, s), 2.49 (3H, s).

Intermediate 31

4-[(E)-2-(dimethylamino)ethenyl]-2-(methylthio)-6-{[1-(phenylsulfonyl)-1H-pyrazol-4-yl]amino}-5-pyrimidinecarbonitrile

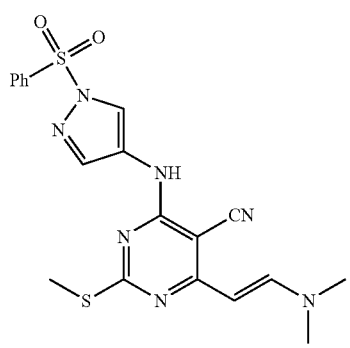 [SMILES: CSc1nc(/C=C/N(C)C)c(C#N)c(Nc2cnn(S(=O)(=O)c3ccccc3)c2)n1]

To a solution of intermediate 29 (4.16 g, 10.8 mmol) in DMF (100 mL) was added tert-butoxy-N,N,N',N'-tetramethylmethanediamine (BBDM, 5.63 g, 32.3 mmol). The mixture was stirred for 16 h at 100° C. After cooling to room temperature, the mixture was poured into ice-water (800 mL), filtered and the solid was washed with water, petroleum and the mixture solvent (petroleum:ethyl acetate=3:1) successively, dried to obtain 4.2 g of product as a yellow solid.

Yield: 64.3%.

MS: $M(C_{19}H_{19}N_7O_2S_2)$=441.54, $(M+1)^+$=442.2.

Intermediate 32

2-(methylthio)-4-(1H-pyrazol-4-ylamino)pyrido[4,3-d]pyrimidin-5(6H)-one

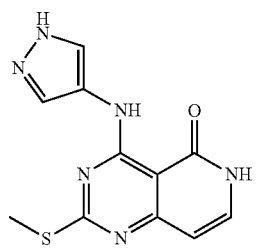 [SMILES: CSc1nc(Nc2cn[nH]c2)c2c(=O)[nH]ccc2n1]

To a suspension of intermediate 31 (4.2 g, 6.94 mmol) in acetic acid (50 mL), HBr (33% in acetic acid, 25 mL) was added slowly (over about 10 min), and the reaction mixture was stirred for 3 h at 40° C. Water (20 mL) was then added, and the mixture was stirred for another 2 h at 80° C. It was cooled and filtered and the solid was treated with saturated $NaHCO_3$ solution, washed with water and dried. The solid was then washed with petroleum ether (3×20 mL)) and ethyl acetate (2×15 mL) and dried to give the desired product as as a light yellow solid (0.8 g, 42.1% yield).

MS: $M(C_{11}H_{10}N_6OS)$=274.31, $(M+1)^+$=275.1

$^1$HNMR (300 mHz, DMSO-$d_6$) δ ppm 12.78 (1H, s), 11.89 (1H, s), 11.62 (1H, s), 8.12 (1H, broad s), 7.87 (1H, broad s), 7.54 (1H, m), 6.29 (1H, d, J=5.4 Hz), 2.49 (3H, s).

Example 12

4-(1H-pyrazol-4-ylamino)-2-[(3R)-3-pyrrolidinylamino]pyrido[4,3-d]pyrimidin-5(6H)-one

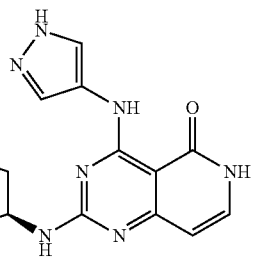

The compound was prepared from intermediate 32 using mCPBA/(R)-3-Amino-1-N-Boc-pyrrolidine and TFA sequences similar to that described for example 1 (Scheme 2).

MS: $M(C_{14}H_{16}N_8O)=312.34$, $(M+1)^+=313.1$

1H NMR (400 MHz, DMSO-$d_6$) δ ppm 1.95-2.07 (m, 1H), 2.17-2.30 (m, 1H), 3.14-3.41 (m, 2H), 3.43-3.54 (m, 1H), 4.47-4.74 (m, 2H), 6.17-6.30 (m, 1H), 7.40-7.71 (m, 1H), 7.97-8.16 (m, 2H), 8.69-8.94 (m, 2H), 11.44-12.17 (m, 2H).

Intermediate 33

4-[(2-methylphenyl)amino]-2-(methylthio)pyrido[4,3-d]pyrimidin-5(6H)-one

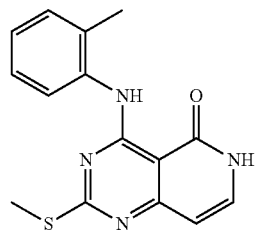 [SMILES: CSc1nc(Nc2ccccc2C)c2c(=O)[nH]ccc2n1]

The compound was prepared from 4-chloro-6-methyl-2-(methylthio)-5-pyrimidinecarbonitrile and 2-methylaniline following a procedure similar to that described for Intermediate 26.

MS: $M(C_{15}H_{14}N_4OS)=298.37$, $(M+1)^+=299.0$

1HNMR (400 mHz, DMSO-$d_6$) δ ppm 11.91 (1H, s), 11.83 (1H, s), 8.28 (1H, d, J=8.0 Hz), 7.60 (1H, d, J=8.0 Hz), 7.28 (1H, t, J=8.0 Hz), 7.07 (1H, t, J=8.0 Hz), 6.34 (1H, J=8.0 Hz), 2.49 (3H, s), 2.34 (3H, s).

Example 13

2-[(3-aminopropyl)amino]-4-[(2-methylphenyl)amino]pyrido[4,3-d]pyrimidin-5(6H)-one

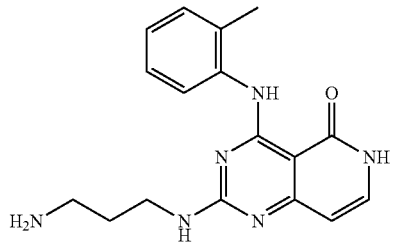 [SMILES: Cc1ccccc1Nc1nc(NCCCN)nc2cc[nH]c(=O)c12]

The compound was prepared from 4-[(2-methylphenyl)amino]-2-(methylthio)pyrido[4,3-d]pyrimidin-5(6H)-one following a procedure (mCPBA/1,1-dimethylethyl (3-aminopropyl)carbamate and TFA) similar to that described for Example 1 (Scheme 2).

MS: $M(C_{17}H_{20}N_6O)=324.39$, $(M+1)^+=325.2$

1HNMR (400 mHz, DMSO-$d_6$) δ ppm 8.20 (1H, m), 7.73 (4H, m), 7.15-7.38 (3H, m), 6.35 (1H, d, J=8.0 Hz), 3.41 (2H, m), 2.83 (2H, m), 2.36 (3H, s), 1.83 (2H, m).

Intermediate 34

4-[(2,2-dioxido-1,3-dihydro-2-benzothien-5-yl)amino]-6-methyl-2-(methylthio)-5-pyrimidinecarbonitrile

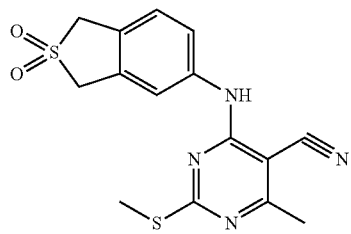 [SMILES: CSc1nc(C)c(C#N)c(Nc2ccc3c(c2)CS(=O)(=O)C3)n1]

The compound was prepared from 4-chloro-6-methyl-2-(methylthio)-5-pyrimidinecarbonitrile and (2,2-dioxido-1,3-dihydro-2-benzothien-5-yl)amine following a procedure similar to that described for Intermediate 23.

MS: $M(C_{15}H_{14}N_4O_2S_2)=346.43$, $(M+1)^+=347.0$

1HNMR (400 MHz, DMSO-$d_6$) δ ppm 9.89 (1H, s), 7.61 (1H, s), 7.55 (1H, dd, J=8.0, 4.0 Hz), 7.36 (1H, d, J=8.0 Hz), 4.50 (2H, s), 4.47 (2H, s), 2.46 (3H, s), 2.49 (3H, s).

Intermediate 35

4-[(2,2-dioxido-1,3-dihydro-2-benzothien-5-yl)amino]-2-(methylthio)pyrido[4,3-d]pyrimidin-5(6H)-one

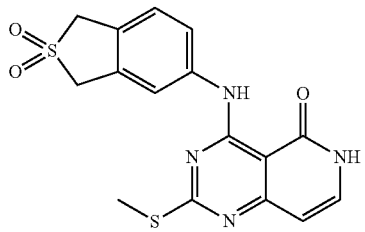 [SMILES: CSc1nc(Nc2ccc3c(c2)CS(=O)(=O)C3)c2c(=O)[nH]ccc2n1]

The compound was prepared from 4-[(2,2-dioxido-1,3-dihydro-2-benzothien-5-yl)amino]-6-methyl-2-(methylthio)-5-pyrimidinecarbonitrile using the procedure as described for intermediate 26. The product was purified using reverse-phase HPLC. HPLC conditions: Gilson using Trilution software, with a phenomenex Luna 5u C18(2) 100A, AXIA, 50×30.00 mm 5 micron, 7.3-minute run (47 mL/min, 14% ACN/$H_2O$, 0.1% TFA to 44% ACN/$H_2O$, 0.1% TFA) with UV detection at 254 nm.

MS: $M(C_{16}H_{14}N_4O_3S_2)=373.44$, $(M+1)^+=374.7$

1HNMR (400 mHz, DMSO-$d_6$) δ ppm 7.88 (1H, s), 7.72 (1H, d, J=8.0 Hz), 7.62 (1H, m), 7.41 (1H, d, J=8.0 Hz), 6.35 (1H, d, J=4.0 Hz), 4.54 (2H, s), 4.48 (2H, s), 2.53 (3H, s).

Example 14

2-[(3-aminopropyl)amino]-4-[(2,2-dioxido-1,3-dihydro-2-benzothien-5-yl)amino]pyrido[4,3-d]pyrimidin-5(6H)-one

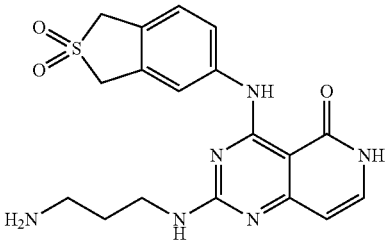 [SMILES: NCCCNc1nc(Nc2ccc3c(c2)CS(=O)(=O)C3)c2c(=O)[nH]ccc2n1]

The compound was prepared from 4-[(2,2-dioxido-1,3-dihydro-2-benzothien-5-yl)amino]-2-(methylthio)pyrido[4,3-d]pyrimidin-5(6H)-one using mCPBA/1,1-dimethylethyl (3-aminopropyl)carbamate and TFA sequences similar to that described for Example 1 (Scheme 2).

MS: $M(C_{18}H_{20}N_6O_3S)=400.46$, $(M+1)^+=400.7$
$^1$HNMR (400 mHz, DMSO-$d_6$) δ ppm 7.30-8.00 (4H, m), 6.24 (1H, m), 4.40-4.60 (4H, m), 3.42 (2H, bs), 2.88 (2H, m), 1.85 (2H, m).

Intermediate 36

N-(3-{[5-cyano-6-methyl-2-(methylthio)-4-pyrimidinyl]amino}phenyl)-1-pyrrolidinecarboxamide

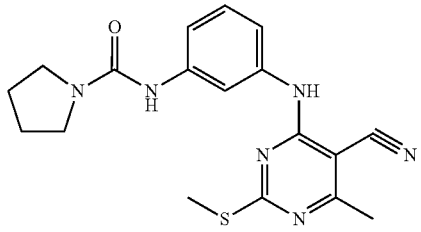 [SMILES: CSc1nc(C)c(C#N)c(Nc2cccc(NC(=O)N3CCCC3)c2)n1]

The compound was prepared from 4-chloro-6-methyl-2-(methylthio)-5-pyrimidinecarbonitrile and N-(3-aminophenyl)-1-pyrrolidinecarboxamide following a procedure similar to that described for Intermediate 23.

MS: $M(C_{18}H_{20}N_6OS)=368.46$, $(M+1)^+=368.7$
$^1$HNMR (400 mHz, DMSO-$d_6$) δ ppm 9.73 (1H, m), 8.13 (1H, s), 7.82 (1H, s), 7.28 (1H, d, J=8.0 Hz), 7.18 (1H, t, J=8.0 Hz), 7.10 (1H, d, J=8.0 Hz), 3.36 (5H, m), 2.44 (3H, s), 2.39 (3H, s), 1.85 (4H, m).

Intermediate 37

N-(3-{[2-(methylthio)-5-oxo-5,6-dihydropyrido[4,3-d]pyrimidin-4-yl]amino}phenyl)-1-pyrrolidinecarboxamide

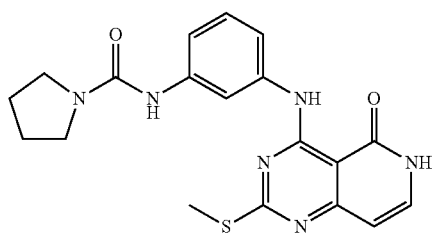 [SMILES: CSc1nc(Nc2cccc(NC(=O)N3CCCC3)c2)c2c(=O)[nH]ccc2n1]

The compound was prepared from N-(3-{[5-cyano-6-methyl-2-(methylthio)-4-pyrimidinyl]amino}phenyl)-1-pyrrolidinecarboxamide using the procedure similar to that described for Intermediate 26. The product was purified using reverse-phase HPLC.

HPLC conditions: Gilson using Trilution software, with a phenomenex Luna 5u C18(2) 100A, AXIA, 50×30.00 mm 5 micron, 7.3-minute run (47 mL/min, 14% ACN/H$_2$O, 0.1% TFA to 44% ACN/H$_2$O, 0.1% TFA) with UV detection at 254 nm.

MS: $M(C_{19}H_{20}N_6O_2S)=396.47$, $(M+1)^+=397.7$
$^1$HNMR (400 mHz, DMSO-$d_6$) δ ppm 8.19 (1H, s), 7.82 (1H, s), 7.59 (2H, m), 7.26 (2H, m), 6.34 (1H, d, J=4.0 Hz), 3.37 (4H, m), 2.54 (3H, s), 1.86 (4H, m).

Example 15

N-[3-({2-[(3-aminopropyl)amino]-5-oxo-5,6-dihydropyrido[4,3-d]pyrimidin-4-yl}amino)phenyl]-1-pyrrolidinecarboxamide

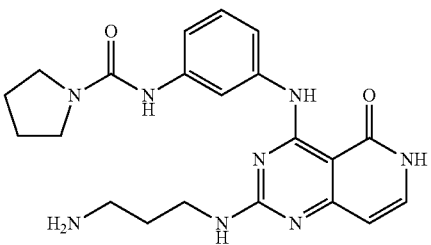 [SMILES: NCCCNc1nc(Nc2cccc(NC(=O)N3CCCC3)c2)c2c(=O)[nH]ccc2n1]

The compound was prepared from N-(3-{[2-(methylthio)-5-oxo-5,6-dihydropyrido[4,3-d]pyrimidin-4-yl]amino}phenyl)-1-pyrrolidinecarboxamide using mCPBA/1,1-dimethylethyl (3-aminopropyl)carbamate and TFA sequences similar to that described for Example 1 (Scheme 2).

MS: $M(C_{21}H_{26}N_8O_2)=422.49$, $(M+1)^+=423.4$
$^1$HNMR (400 mHz, DMSO-$d_6$) δ ppm 8.27 (1H, s), 8.21 (1H, s), 7.73 (4H, m), 7.29 (3H, m), 6.34 (1H, d, J=8.0 Hz), 3.62 (2H, m), 3.38 (4H, m), 2.89 (2H, m), 1.87 (6H, m).

Example 16

N-{3-[(2-{[2-(1H-imidazol-4-yl)ethyl]amino}-5-oxo-5,6-dihydropyrido[4,3-d]pyrimidin-4-yl)amino]phenyl}-1-pyrrolidinecarboxamide

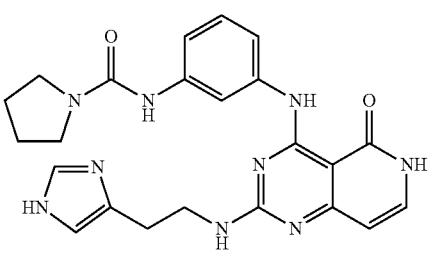 [SMILES: O=C(Nc1cccc(Nc2nc(NCCc3c[nH]cn3)nc3cc[nH]c(=O)c23)c1)N1CCCC1]

To a solution of N-(3-{[2-(methylthio)-5-oxo-5,6-dihydropyrido[4,3-d]pyrimidin-4-yl]amino}phenyl)-1-pyrrolidinecarboxamide (80 mg, 0.26 mmol) in DMF (3 mL) was added m-CPBA (102 mg, 0.59 mmol), and the reaction mixture was stirred overnight. Histamine (230 mg, 2.08 mmol) was added and the reaction mixture was stirred for 5 h. It was then concentrated and the residue was subjected to reverse-phase HPLC purification to afford the product (75 mg).

HPLC conditions: Gilson using Trilution software, with a phenomenex Luna 5u C18(2) 100A, AXIA, 50×30.00 mm 5 micron, 7.3-minute run (47 mL/min, 3% ACN/H$_2$O, 0.1% TFA to 33% ACN/H$_2$O, 0.1% TFA) with UV detection at 254 nm.

MS: (C$_{23}$H$_{25}$N$_9$O$_2$=459.51, m/z (M+1) 460.1

$^1$HNMR (400 mHz, DMSO-d$_6$) δ ppm 8.96 (1H, m), 7.20-8.50 (5H, m)), 6.30 (1H, m), 3.78 (2H, m), 3.36 (4H, m), 2.98 (2H, m), 1.86 (4H, m).

Example 17

N-[3-({5-oxo-2-[(3R)-3-pyrrolidinylamino]-5,6-dihydropyrido[4,3-d]pyrimidin-4-yl}amino)phenyl]-1-pyrrolidinecarboxamide

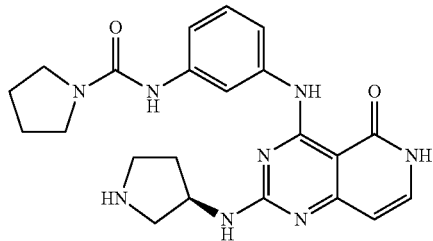 [SMILES: O=C(Nc1cccc(Nc2nc(N[C@@H]3CCNC3)nc3cc[nH]c(=O)c23)c1)N1CCCC1]

The compound was prepared from N-(3-{[2-(methylthio)-5-oxo-5,6-dihydropyrido[4,3-d]pyrimidin-4-yl]amino}phenyl)-1-pyrrolidinecarboxamide using m-CPBA/1,1-dimethylethyl (3-aminopropyl)carbamate and TFA sequences similar to that described for Example 1 (Scheme 2).

MS: M(C$_{22}$H$_{26}$N$_8$O$_2$)=434.50, (M+1)$^+$=435.2

$^1$HNMR (400 mHz, DMSO-d$_6$) δ ppm 7.20-8.50 (6H, m), 6.23 (1H, m), 3.10-3.80 (9H, m), 2.20-2.40 (2H, m), 1.86 (4H, m).

Intermediate 38

N-(4-{[5-cyano-6-methyl-2-(methylthio)-4-pyrimidinyl]amino}phenyl)-1-pyrrolidinecarboxamide

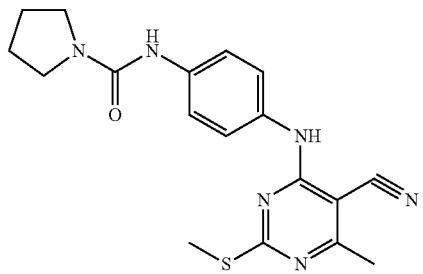 [SMILES: CSc1nc(C)c(C#N)c(Nc2ccc(NC(=O)N3CCCC3)cc2)n1]

The compound was prepared from 4-chloro-6-methyl-2-(methylthio)-5-pyrimidinecarbonitrile and N-(4-aminophenyl)-1-pyrrolidinecarboxamide following procedure similar to that described for Intermediate 23.

MS: M(C$_{18}$H$_{20}$N$_6$OS)=368.36, m/z (M+1)$^+$=369.0

$^1$HNMR (400 mHz, DMSO-d$_6$) δ ppm 9.64 (1H, s), 8.13 (1H, s), 7.48 (2H, d, J=8.0 Hz), 7.37 (2H, d, J=8.0 Hz), 3.36 (4H, m), 2.43 (3H, s), 2.37 (3H, s), 1.85 (4H, m).

Intermediate 39

N-(4-{[2-(methylthio)-5-oxo-5,6-dihydropyrido[4,3-d]pyrimidin-4-yl]amino}phenyl)-1-pyrrolidinecarboxamide

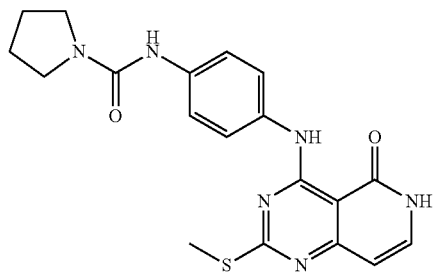 [SMILES: CSc1nc(Nc2ccc(NC(=O)N3CCCC3)cc2)c2c(=O)[nH]ccc2n1]

The compound was prepared from N-(4-{[5-cyano-6-methyl-2-(methylthio)-4-pyrimidinyl]amino}phenyl)-1-pyrrolidinecarboxamide using the procedure similar to that described for Intermediate 26.

MS: M(C$_{19}$H$_{20}$N$_6$O$_2$S)=396.47, m/z (M+1)=397.1 and 398.1

$^1$HNMR (400 mHz, DMSO-d$_6$) δ ppm 8.16 (1H, s), 7.61 (2H, d, J=8.0 Hz), 7.54 (1H, d, J=8.0 Hz), 6.32 (1H, d, J=8.0 Hz), 3.37 (4H, m), 1.85 (4H, m).

Example 18

N-[4-({2-[(3-aminopropyl)amino]-5-oxo-5,6-dihydropyrido[4,3-d]pyrimidin-4-yl}amino)phenyl]-1-pyrrolidinecarboxamide

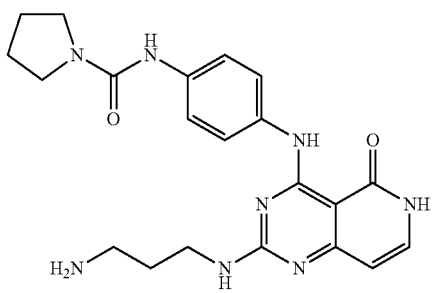 [SMILES: NCCCNc1nc(Nc2ccc(NC(=O)N3CCCC3)cc2)c2c(=O)[nH]ccc2n1]

The compound was prepared from N-(4-{[2-(methylthio)-5-oxo-5,6-dihydropyrido[4,3-d]pyrimidin-4-yl]amino}phenyl)-1-pyrrolidinecarboxamide using mCPBA/1,1-dimethylethyl (3-aminopropyl)carbamate and TFA sequences as described for Example 1 (Scheme 2).

MS: M(C$_{21}$H$_{26}$N$_8$O$_2$)=422.49, m/z (M+1)=423.0

$^1$HNMR (400 mHz, DMSO-d$_6$) δ ppm 8.25 (1H, s), 7.50-7.80 (8H, m), 6.32 (1H, d, J=8.0 Hz), 3.47 (2H, m), 3.37 (4H, m), 2.87 (2H, m), 1.86 (6H, m).

The following 2-[(3-aminopropyl)amino]-4-[(substituted)amino]pyrido[4,3d]pyrimidin-5(6H)-one were prepared from 4-chloro-6-methyl-2-(methylthio)-5-pyrimidinecarbonitrile and appropriate anilines following the same synthetic route as described for Example 1 (Scheme 2).

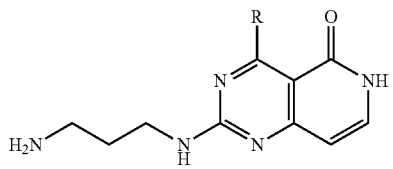
| Ex. No. | R | MS | (M + H)+ (m/z) | NMR (400 mHz) δ ppm |
|---|---|---|---|---|
| 19 | 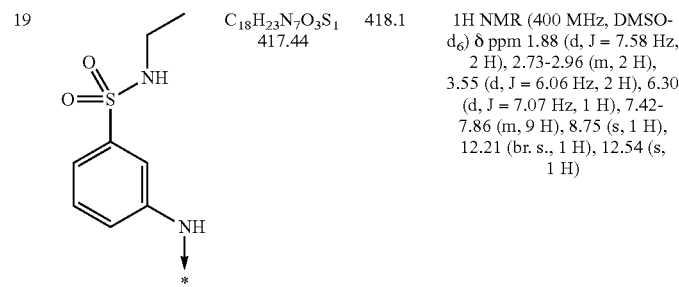 | C₁₈H₂₃N₇O₃S₁ 417.44 | 418.1 | 1H NMR (400 MHz, DMSO-d₆) δ ppm 1.88 (d, J = 7.58 Hz, 2 H), 2.73-2.96 (m, 2 H), 3.55 (d, J = 6.06 Hz, 2 H), 6.30 (d, J = 7.07 Hz, 1 H), 7.42-7.86 (m, 9 H), 8.75 (s, 1 H), 12.21 (br. s., 1 H), 12.54 (s, 1 H) |
| 20 | 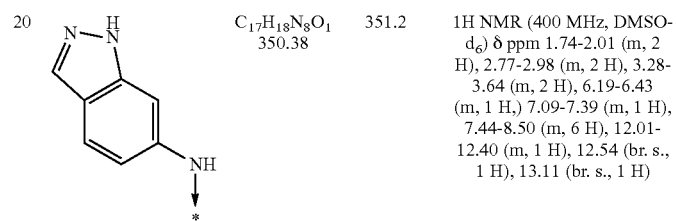 | C₁₇H₁₈N₈O₁ 350.38 | 351.2 | 1H NMR (400 MHz, DMSO-d₆) δ ppm 1.74-2.01 (m, 2 H), 2.77-2.98 (m, 2 H), 3.28-3.64 (m, 2 H), 6.19-6.43 (m, 1 H,) 7.09-7.39 (m, 1 H), 7.44-8.50 (m, 6 H), 12.01-12.40 (m, 1 H), 12.54 (br. s., 1 H), 13.11 (br. s., 1 H) |
| 21 | 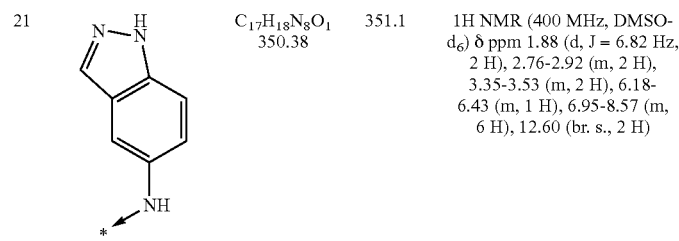 | C₁₇H₁₈N₈O₁ 350.38 | 351.1 | 1H NMR (400 MHz, DMSO-d₆) δ ppm 1.88 (d, J = 6.82 Hz, 2 H), 2.76-2.92 (m, 2 H), 3.35-3.53 (m, 2 H), 6.18-6.43 (m, 1 H), 6.95-8.57 (m, 6 H), 12.60 (br. s., 2 H) |
| 22 | 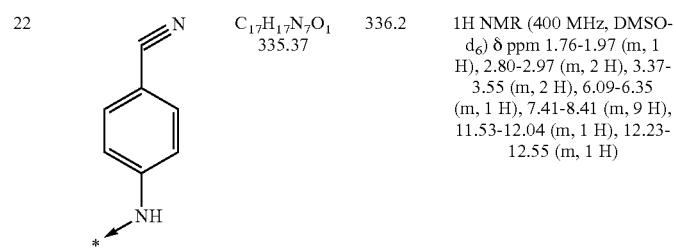 | C₁₇H₁₇N₇O₁ 335.37 | 336.2 | 1H NMR (400 MHz, DMSO-d₆) δ ppm 1.76-1.97 (m, 1 H), 2.80-2.97 (m, 2 H), 3.37-3.55 (m, 2 H), 6.09-6.35 (m, 1 H), 7.41-8.41 (m, 9 H), 11.53-12.04 (m, 1 H), 12.23-12.55 (m, 1 H) |

Intermediate 40

8-bromo-4-[(3-methylphenyl)amino]-2-(methylthio) pyrido[4,3-d]pyrimidin-5(6H)-one

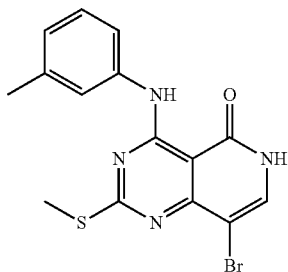 [SMILES: CSc1nc(Nc2cccc(C)c2)c2c(=O)[nH]cc(Br)c2n1]

4-[(3-methylphenyl)amino]-2-(methylthio)pyrido[4,3-d] pyrimidin-5(6H)-one (500 mg, 1.676 mmol) was dissolved into N,N-Dimethylformamide (DMF) (8 mL) and NBS (298 mg, 1.676 mmol) was added. The reaction mixture was stirred at rt for 2 h. It was quenched with water (12 mL) and EtOAc (5 mL) was added. The mixture was filtered to collect the precipitate, which was further dried under high vacuum to give 470 mg of crude product (83% pure based on LC-MS).

MS: $M(C_{15}H_{13}BrN_4OS)=377.26$, $(M+1)^+=377.2$ and 379.2

$^1$HNMR (400 mHz, DMSO-$d_6$) δ ppm 12.31 (1H, d, J=4.0 Hz), 12.04 (1H, s), 8.01 (1H, d, J=4.0 Hz), 7.61 (1H, s), 7.58 (1H, d, J=8.0 Hz), 7.30 (1H, t, J=8.0 Hz), 6.98 (1H, d, J=8.0 Hz), 2.58 (3H, s), 2.33 (3H, s).

Example 23

2-[(3-aminopropyl)amino]-8-bromo-4-[(3-methylphenyl)amino]pyrido[4,3-d]pyrimidin-5(6H)-one

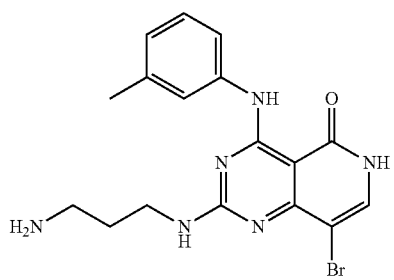 [SMILES: Cc1cccc(Nc2nc(NCCCN)nc3c(Br)c[nH]c(=O)c23)c1]

The product was prepared from 8-bromo-4-[(3-methylphenyl)amino]-2-(methylthio)pyrido[4,3-d]pyrimidin-5(6H)-one using mCPBA/1,1-dimethylethyl (3-aminopropyl)carbamate and TFA sequences similar that described for Example 1 (Scheme 2). It was purified using reverse-phase HPLC.

MS: $M(C_{17}H_{19}BrN_6O)=403.28$, $(M+1)^+=402.7$ and 404.9

$^1$HNMR (400 mHz, DMSO-$d_6$) δ ppm 7.60-7.80 (6H, m), 7.55 (1H, m), 7.26 (1H, m), 6.95 (1H, m), 3.47 (2H, m), 2.87 (2H, m), 2.34 (3H, s), 1.88 (2H, m).

Intermediate 41

4-[(3-methylphenyl)amino]-2-(methylsulfonyl)pyrido[4,3-d]pyrimidin-5(6H)-one

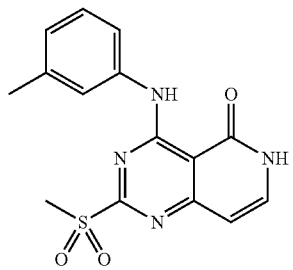 [SMILES: Cc1cccc(Nc2nc(S(C)(=O)=O)nc3cc[nH]c(=O)c23)c1]

A solution of 4-[(3-methylphenyl)amino]-2-(methylthio) pyrido[4,3-d]pyrimidin-5(6H)-one (0.500 g, 1.6 mmol) in 20 mL of N,N-Dimethylformamide (DMF) was added a 40 mL scintillation vial equipped with a magnetic stir bar. A solution of m-CPBA (0.723 g, 4.19 mmol) in DMF (5 mL) was introduced dropwise over 5 min and the reaction mixture was stirred at room temperature for 4 h. LC-MS analysis revealed that the all starting material was converted to the desired sulfone intermediate. This crude sulfone solution in DMF was carried on to final product formation following a procedure similar to that described in the example section.

MS: $M(C_{15}H_{14}N_4O_3S)=330.36$, $(M+H)=330.7$

Example 24

2-{[3-(dimethylamino)propyl]amino}-4-[(3-methylphenyl)amino]pyrido[4,3-d]pyrimidin-5(6H)-one

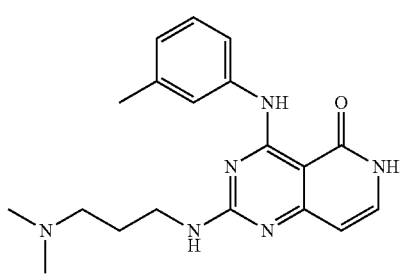 [SMILES: Cc1cccc(Nc2nc(NCCCN(C)C)nc3cc[nH]c(=O)c23)c1]

Intermediate 41 (50 mg, 0.17 mmol) in DMF was added to a 20 mL scintillation vial containing N,N-dimethyl-1,3-propanediamine (1.7 mmol) and a magnetic stir bar. The reaction mixture was stirred for 1 hour, and then DMF was removed under vacuum. The residue was dissolved in methanol and loaded to the top of an SCX cartridge. It was eluted with methanol until all of the chlorobenzoic acid came off and then with 2N $NH_3$ in methanol to get off product. Fractions containing product were concentrated and purified via reverse-phase HPLC utilizing a Phenomenex Luna 5u C18 column eluting with acetonitrile, water, trifluoroacetic acid to afford the product as a TFA salt.

MS: $M(C_{16}H_{22}N_6O)=352$, $(M+H)^+=353$

1H NMR (400 MHz, DMSO-$d_6$) δ ppm 1.93-2.06 (m, 2H), 2.36 (s, 3H), 2.76 (d, J=4.29 Hz, 6H), 3.11 (m, 2H), 3.50 (q, J=6.1 Hz, 2H), 6.36 (d, J=7.1 Hz, 1H), 7.08 (d, J=7.3 Hz, 1H), 7.36 (t, J=7.8 Hz, 1H), 7.59 (d, J=8.34 Hz, 2H), 7.83 (t, J=6.7 Hz, 1H), 9.39 (br. s., 1H), 12.39 (s, 1H), 12.56 (d, J=5.8 Hz, 1H).

The following 4-[(3-methylphenyl)amino]-2-{[amino substituted}pyrido[4,3-d]pyrimidin-5(6H)-one compounds were prepared from 44(3-methylphenyl)amino]-2-(methylsulfonyl)pyrido[4,3-d]pyrimidin-5(6H)-one (Intermediate 41) and the corresponding amines following the procedure of Example 24.

Example 28

4-[(3-methylphenyl)amino]-2-{[2-(4-pyridinyl)ethyl]amino}pyrido[4,3-d]pyrimidin-5(6H)-one

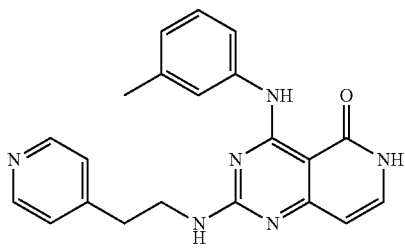

Intermediate 41 (70 mg, 0.212 mmol) in DMF was added to a 20 mL scintillation vial containing 2-(4-pyridinyl)ethanamine (259 mg, 2.1 mmol) and a magnetic stir bar. The reaction mixture was stirred for 1 h and DMF was removed under vacuum. The residue was purified via reverse-phase HPLC utilizing a Phenomenex Luna 5u C18 column eluting with acetonitrile, water, trifluoroacetic acid to afford the product as a TFA salt.

MS: $M(C_{21}H_{20}N_6O)=372.43$ $(M+H)^+=373.0$

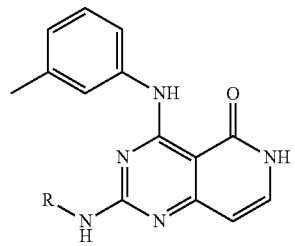

| Example # | R | Mass (M + H) | NMR |
|---|---|---|---|
| 25 | ![N-methyl-N'-methylpropane-1,3-diamine] | 367 | ¹H NMR (400 MHz, DMSO-$d_6$) δ ppm 1.98 (d, J = 7.1 Hz, 2 H), 2.34 (br. s., 3 H), 2.69-2.84 (m, 5 H), 3.07 (br. s., 2 H), 3.20 (s, 3 H), 3.72 (br. s., 2 H), 6.19-6.42 (m, 1 H), 6.90-7.04 (m, 1 H), 7.22-7.39 (m, 1 H), 7.48 (br. s., 1 H), 7.53-7.68 (m, 2 H,) 9.45 (br. s., 1 H), 11.58 (br. s., 1 H), 11.98-12.12 (m, 1 H) |
| 26 | ![N-methylpropane-1,3-diamine] | 339 | ¹H NMR (400 MHz, DMSO-$d_6$) δ ppm 1.87 (m, 3 H), 2.33 (d, J = 1.8 Hz, 1 H), 2.36 (s, 3 H), 2.91-2.99 (m, 4 H), 3.45 (m, 3 H), 3.77 (br. s., 1 H), 6.26 (m, 1 H), 7.04 (d, 1 H), 7.34 (t, J = 7.8 Hz, 1 H), 7.59 (d, J = 7.8 Hz, 1 H), 7.62 (s, 1 H), 8.39 (br. s., 1 H), 12.28 (br. s., 1 H) |
| 27 | ![3-morpholinopropylamine] | 395 | ¹H NMR (400 MHz, DMSO-$d_6$) δ ppm 1.98 (br. s., 4 H), 2.32-2.34 (m, 2 H), 2.35 (s, 3 H), 2.67 (t, J = 1.9 Hz, 1 H), 2.00 (m, 2 H), 3.17 (s, 3 H), 3.57 (br. s., 1 H), 3.94 (br. s., 2 H), 6.23 (br. s., 1 H), 7.00 (s, 1 H), 7.33 (s, 1 H), 7.50 (m, 1 H), 7.60 (br. s., 2 H), 11.93 (m, 1 H), 12.20 (s, 1 H) |

1H NMR (400 MHz, DMSO-d₆) δ ppm 2.30 (s, 3H), 2.34 (s, 1H), 3.10 (t, J=6.8 Hz, 2H), 3.74 (q, J=6.6 Hz, 2H), 6.34 (d, J=6.8 Hz, 1H), 7.07 (d, J=7.6 Hz, 1H), 7.32 (t, J=8.2 Hz, 1H), 7.53-7.58 (m, 2H), 7.65 (d, J=6.1 Hz, 2H), 7.77 (t, J=6.8 Hz, 1H), 8.68 (d, J=6.3 Hz, 2H), 8.74 (d, J=6.1 Hz, 1H), 12.31 (s, 1H).

The following 4-[(3-methylphenyl)amino]-2-{[amino substituted}pyrido[4,3-d]pyrimidin-5(6H)-one compounds were prepared from 44(3-methylphenyl)amino]-2-(methylsulfonyl)pyrido[4,3-d]pyrimidin-5(6H)-one and the corresponding amine following the procedure similar to that described for Example 28.

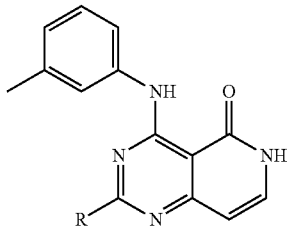

| Example # | R | Mass M + H | NMR |
|---|---|---|---|
| 29 | ![1-methylpiperidin-4-yl-NH-*] | 365 | ¹H NMR (400 MHz, DMSO-d₆) δ ppm 1.75 (m, 2 H), 2.20 (br. s., 2 H), 2.34 (s, 3 H), 2.36 (s, 3 H), 2.80 (t, J = 4.0 Hz, 4 H), 3.11 (m, 1 H), 3.52 (br. s., 1 H), 6.24 (br. s., 1 H), 7.04 (d, J = 7.6 Hz, 1 H), 7.36 (t, J = 7.8 Hz, 1 H), 7.47 (s, 1 H), 7.64 (br. s., 2 H), 11.93 (m, 1 H) 12.25 (br. s., 1 H) |
| 30 | ![4-sulfamoylphenethyl-NH-*] | 451 | ¹H NMR (400 MHz, DMSO-d₆) δ ppm 2.30 (s, 3 H), 2.33 (d, J = 1.7 Hz, 1 H), 2.96 (t, J = 7.6 Hz, 3 H), 3.65 (m, 4 H), 6.35 (d, J = 6.6 Hz, 1 H), 7.08 (d, J = 7.3 Hz, 1 H), 7.34 (t, J = 7.2 Hz, 3 H), 7.55 (t, J = 8.1 Hz, 2 H), 7.70 (dd, J = 2.1, 1.1 Hz, 2 H), 7.90 (dt, J = 3.8, 2.0 Hz, 2 H), 12.31 (br. s., 1 H) |
| 31 | ![1H-imidazol-2-yl-ethyl-NH-*] | 381.8 | ¹HNMR (400 MHz, DMSO-d₆) 9.00 (1H, s), 8.85 (1H, m), 7.45-7.95 (5H, m), 7.30 (1H, m), 7.04 (1H, m), 6.34 (1H, d, J = 8.0 Hz) 3.01 (2H, m), 2.30 (3H, s). |
| 32 | ![4-aminocyclohexyl-NH-*] | 365 | ¹H NMR (400 MHz, DMSO-d₆) δ ppm 1.74 (br. s., 6 H), 1.91 (br. s., 2 H), 2.33 (d, J = 1.8 Hz, 3 H), 3.20 (d, J = 6.6 Hz, 2 H), 3.96 (br. s., 1 H), 6.27 (br. s., 1 H), 7.01 (d, J = 7.1 Hz, 1 H), 7.30 (t, J = 8.1 Hz, 1 H), 7.53 (d, J = 8.8 Hz, 1 H), 7.67 (br. s., 2 H), 7.81 (br. s., 3 H), 12.25 (br. s., 1 H) |

-continued

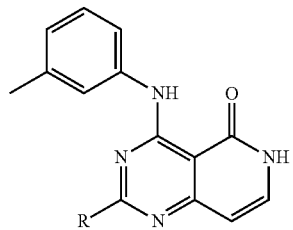

| Example # | R | Mass M + H | NMR |
|---|---|---|---|
| 33 | H₂N-cyclohexyl-NH-* | 365 | ¹H NMR (400 MHz, DMSO-d₆) δ ppm 1.19 (m, 2 H), 1.32 (m, 2 H), 1.89 (m, 3 H), 2.19 (d, J = 11.6 Hz, 1 H), 2.34 (s, 3 H), 3.07 (dd, J = 8.0, 3.7 Hz, 1 H), 3.36 (d, J = 11.87 Hz, 2 H), 3.93 (m, 1 H), 6.12 (d, J = 7.3 Hz, 1 H), 6.90 (t, J = 8.8 Hz, 1 H), 7.26 (t, J = 7.8 Hz, 1 H), 7.37 (t, J = 3.5 Hz, 1 H), 7.53 (d, J = 8.3 Hz, 1 H), 7.68 (d, J = 7.8 Hz, 1 H), 7.81 (d, 1 H), 11.89 (s, 1 H), 11.97 (s, 1 H) |
| 34 | H₂N-C(CH₃)₂-CH₂-NH-* | 353 | ¹H NMR (400 MHz, DMSO-d₆) δ ppm 0.99 (s, 6 H), 2.34 (s, 2 H), 2.37 (s, 3 H), 2.76 (q, 1 H), 3.26 (d, J = 6.1 Hz, 1 H), 3.42 (d, J = 6.1 Hz, 2 H), 3.74 (br. s., 1 H), 6.30 (d, J = 7.1 Hz, 1 H), 7.06 (d, J = 7.3 Hz, 1 H), 7.34 (t, J = 7.8 Hz, 1 H), 7.50 (d, J = 5.1 Hz, 2 H), 7.70 (br. s., 1 H), 7.93 (br. s., 1 H), 12.29 (br. s., 1 H) |
| 35 | pyrrolidinone-propyl-NH-* | 393 | ¹H NMR (400 MHz, DMSO-d₆) δ ppm 1.88 (m, 4 H) 2.17 (t, J = 8.1 Hz, 2 H) 2.36 (s, 3 H) 3.28 (m, 4 H) 3.40 (d, J = 6.32 Hz, 2 H) 6.36 (d, J = 7.1 Hz, 1 H) 7.06 (d, J = 7.3 Hz, 1 H) 7.35 (t, J = 7.8 Hz, 1 H) 7.58 (s, 2 H) 7.77 (t, J = 6.7 Hz, 1 H) 8.52 (br. s., 1 H) 12.36 (m, 2 H) |
| 36 | H₂N-C(CH₃)₂-CH₂-NH-* | 339 | ¹H NMR (400 MHz, DMSO-d₆) δ ppm 1.28 (s, 6 H), 2.36 (d, J = 0.2 Hz, 2 H), 3.53 (d, J = 6.1 Hz, 1 H), 6.29 (d, J = 6.8 Hz, 0 H), 6.92 (d, J = 7.3 Hz, 0 H), 7.23 (s, 1 H), 7.5 (m, 1 H), 7.8 (m, 2 H), 8.04 (br. s., 2 H), 9.08 (br. s., 1 H), 11.80 (m, 1 H) |
| 37 | CH₃-NH-* | 282 | ¹H NMR (400 MHz, DMSO-d₆) δ ppm 2.35 (s, 3 H), 2.93 (m, 3 H), 3.61 (br. s., 1 H), 6.36 (d, J = 6.8 Hz, 1 H), 7.05 (d, J = 7.6 Hz, 1 H), 7.33 (t, J = 7.7 Hz, 1 H), 7.61 (m, 2 H), 7.75 (br. s., 1 H), 8.32 (br. s., 1 H), 12.38 (br. s., 1 H) |
| 38 | HN-* | 268 | ¹H NMR (400 MHz, DMSO-d₆) δ ppm 2.33 (s, 3 H), 3.85 (m, 1 H), 6.19 (m, 1 H), 6.95 (m, 1 H), 7.21 (m, 1 H), 7.58 (m, 1 H), 7.32 (m, 2 H), 11.31 (m, 1 H), 11.95 (m, 2 H) |
| 39 | H₂N-CH₂-CH(OH)-CH₂-NH-* | 341 | ¹H NMR (400 MHz, DMSO-d₆) δ ppm 2.36 (s, 3 H), 2.68 (m, 1 H), 2.99 (d, J = 4.6 Hz, 1 H), 3.48 (m, 2 H), 3.95 (m, 1 H), 5.79 (br. s., 1 H), 6.36 (d, J = 7.1 Hz, 1 H), 7.06 (d, J = 7.6 Hz, 1 H), 7.34 (t, J = 7.71 Hz, 1 H), 7.58 (d, J = 8.6 Hz, 2 H), 7.79 (t, J = 6.7 Hz, 1 H), 7.90 (br. s., 2 H), 9.15 (br. s., 1 H), 12.38 (s, 1 H), 12.45 (br. s., 1 H) |

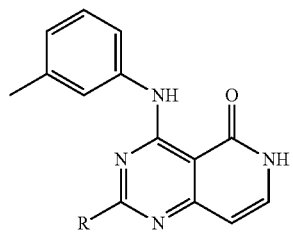

| Example # | R | Mass M + H | NMR |
|---|---|---|---|
| 40 | 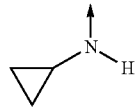 | 308 | $^1$H NMR (400 MHz, DMSO-d$_6$) δ ppm 0.70 (m, 2 H), 0.88 (m, 2 H), 2.33 (br. s., 3 H), 2.84 (dt, J = 6.9, 3.5 Hz, 1 H), 7.01 (d, J = 7.6 Hz, 1 H), 7.30 (t, J = 7.71 Hz, 1 H), 7.74 (t, J = 6.7 Hz, 1 H), 7.69 (d, J = 7.6 Hz, 1 H), 7.81 (br. s., 1 H), 12.38 (br. s., 1 H) |

The following compounds were prepared from 4-[(3-methylphenyl)amino]-2-(methylsulfonyl)pyrido[4,3-d]pyrimidin-5(6H)-one using mCPBA/1,1-dimethylethyl (3-aminopropyl)carbamate and TFA sequence similar to that described for Example 1 (Scheme 2).

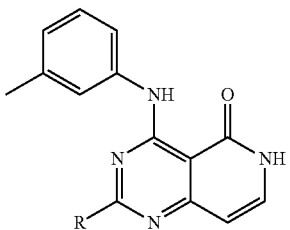

| Example # | R | Mass M + H | NMR |
|---|---|---|---|
| 41 | 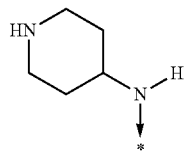 | 351 | $^1$H NMR (400 MHz, DMSO-d$_6$) δ ppm 1.59 (m, 2 H), 2.01 (m, 2 H), 2.36 (s, 3 H), 2.90 (m, 2 H), 3.20 (m, 1 H), 3.35 (m, 1 H), 4.19 (m, 1 H), 6.21 (br. s., 1 H), 6.90 (br. s., 1 H), 7.29 (m, 1 H), 7.49 (m, 1 H), 7.55 (m, 1 H), 7.75 (m, 1 H), 8.67 (m, 2 H), 12.17 (m, 2 H) |
| 42 | 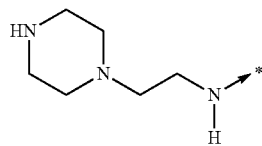 | 380 | $^1$H NMR (400 MHz, DMSO-d$_6$) δ ppm 2.33 (s, 3 H), 2.45 (t, J = 7.2 Hz, 1 H), 2.67 (d, J = 1.8 Hz, 2 H), 3.17 (d, J = 5.3 Hz, 1 H), 3.34 (s, 2 H), 3.45 (m, 2 H), 6.04 (d, J = 7.3 Hz, 1 H), 6.13 (d, J = 7.33 Hz, 1 H), 6.90 (d, J = 7.6 Hz, 2 H), 7.22 (t, J = 7.83 Hz, 2 H), 7.38 (m, 2 H), 7.60 (d, J = 8.3 Hz, 1 H), 7.65 (s, 2 H), 7.73 (d, J = 7.3 Hz, 1 H), 11.85 (s, 1 H), 11.95 (s, 1 H) |
| 43 | 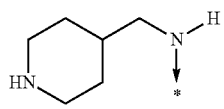 | 365 | $^1$H NMR (400 MHz, DMSO-d$_6$) δ ppm 1.31 (m, 2 H), 1.89 (m, 3 H), 2.36 (s, 3 H), 2.84 (m, 2 H), 3.30 (m, 4 H), 3.56 (m, 1 H), 6.27 (m, 1 H), 7.05 (m, 1 H), 7.38 (m, 1 H), 7.54 (m, 2 H), 7.70 (m, 1 H), 8.19 (m, 1 H), 8.46 (m, 1 H), 12.30 (m, 1 H) |

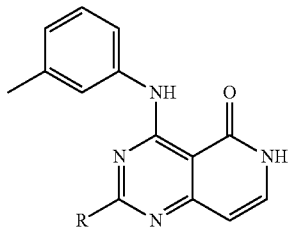

| Example # | R | Mass M + H | ¹H NMR |
|---|---|---|---|
| 44 | (HN-pyrrolidin-3-yl)NH— | 337 | ¹H NMR (400 MHz, DMSO-d₆) δ ppm 1.11 (s, 1 H), 1.99 (m, 1 H), 2.29 (m, 2 H), 2.37 (s, 3 H), 3.47 (d, J = 12.1 Hz, 1 H), 4.56 (d, J = 4.80 Hz, 1 H), 6.34 (s, 1 H), 7.09 (d, J = 7.6 Hz, 1 H), 7.36 (m, 1 H), 7.58 (m, 2 H), 7.80 (m, 1 H), 8.98 (br. s., 2 H), 9.62 (br. s., 1 H), 12.41 (s, 1 H), 12.51 (br. s., 1 H) |
| 45 | (piperidin-3-yl)NH— | 351 | ¹H NMR (400 MHz, DMSO-d₆) δ ppm 1.67 (m, 2 H), 2.07 (m, 2 H), 2.34 (br. s., 2 H), 2.36 (s, 3 H), 2.89 (m, 2 H), 3.18 (d, 1 H), 3.39 (t, J = 12.1 Hz, 1 H), 4.18 (m, 1 H), 6.25 (d, J = 5.6 Hz, 1 H), 7.04 (d, J = 7.1 Hz, 1 H), 7.33 (t, J = 7.8 Hz, 1 H), 7.50 (m, 2 H), 8.69 (br. s., 2 H), 12.24 (br. s., 1 H) |
| 46 | 4-(aminomethyl)piperidin-1-yl | 365 | ¹H NMR (400 MHz, DMSO-d₆) δ ppm 1.24 (m, 2 H), 1.88 (m, 1 H), 2.32 (m, 3 H), 2.73 (m, 2 H), 3.01 (m, 2 H), 3.98 (br. s., 2 H), 4.66 (d, J = 12.1 Hz, 2 H), 6.30 (br. s., 1 H), 6.97 (d, J = 6.6 Hz, 1 H), 7.28 (t, J = 7.7 Hz, 1 H), 7.58 (m, 3 H), 7.80 (br. s., 2 H), 11.98 (m, 2 H) |
| 47 | (3R)-3-aminopyrrolidin-1-yl | 337 | ¹H NMR (400 MHz, DMSO-d₆) δ ppm 1.40 (d, J = 1.8 Hz, 2 H), 2.13 (br. s., 1 H), 2.35 (d, J = 5.0 Hz, 3 H), 3.52 (m, 1 H), 3.74 (m, 3 H), 4.00 (br. s., 1 H), 6.53 (m, 1 H), 7.03 (dd, J = 13.3, 7.71 Hz, 1 H), 7.29 (t, J = 8.1 Hz, 1 H), 7.6 (m, 2 H), 8.18 (br. s., 2 H), 12.29 (m, 1 H), 12.43 (m, 1 H) |
| 48 | (3S)-3-aminopyrrolidin-1-yl | 337 | ¹H NMR (400 MHz, DMSO-d₆) δ ppm 1.40 (d, J = 1.8 Hz, 2 H), 2.14 (d, J = 6.8 Hz, 1 H), 2.35 (d, J = 6.3 Hz, 3 H), 3.51 (m, 1 H), 3.74 (m, 3 H), 4.01 (br. s., 1 H), 6.53 (m, 1 H), 7.03 (t, J = 9.0 Hz, 1 H), 7.30 (m, 1 H), 7.65 (m, 3 H), 8.21 (br. s., 2 H), 12.27 (br. s., 1 H) |
| 49 | (pyrrolidin-3-yl)NH— | 337 | ¹HNMR (400 mHz, DMSO-d₆) δ ppm 8.86 (2H, m), 7.40-7.90 (3H, m), 7.30 (1H, m), 7.01 (1H, m), 6.22 (1H, d, J = 8.0 Hz), 4.54 (1H, m), 3.44 (1H, m), 3.30 (3H, m), 2.35 (3H, m), 2.25 (1H, m), 2.05 (1H, m). |
| 50 | (piperidin-3-ylmethyl)NH— | 365 | ¹HNMR (400 mHz, DMSO-d₆) δ 8.62 (1H, m), 8.29 (1H, m), 7.50-7.80 (3H, m), 7.33 (1H, m), 7.04 (1H, m), 6.29 (1H, d, J = 8.0 Hz), 3.44 (1H, m), 3.26 (3H, m), 2.77 (1H, m), 2.63 (1H, m), 2.36 (3H, s), 2.09 (1H, m), 1.80 (2H, m), 1.58 (1H, m), 1.26 (1H, m). |

Example 51

N[1]-[3-({4-[(3-methylphenyl)amino]-5-oxo-5,6-dihydropyrido[4,3-d]pyrimidin-2-yl}amino)propyl]-1,1-cyclopropanedicarboxamide

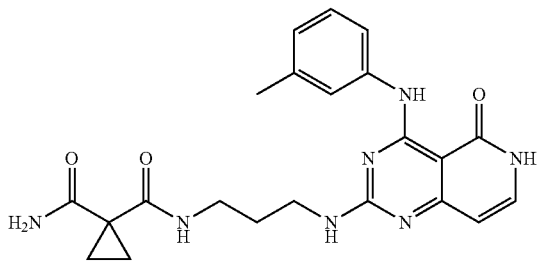 [SMILES: Cc1cccc(Nc2nc(NCCCNC(=O)C3(C(N)=O)CC3)nc3cc[nH]c(=O)c23)c1]

To a solution of 2-[(3-aminopropyl)amino]-4-[(3-methylphenyl)amino]pyrido[4,3-d]pyrimidin-5(6H)-one (60 mg, 0.137 mmol) in DMF (1 mL) were added 1-(aminocarbonyl)cyclopropanecarboxylic acid (19.44 mg, 0.151 mmol), EDC (31.5 mg, 0.164 mmol), HOBT (41.9 mg, 0.274 mmol), 4-methylmorpholine (0.075 mL, 0.684 mmol), and the reaction mixture was stirred for 2 h. The reaction was quenched with water (2 mL), extracted with EtOAc (3×5 mL). The extract was dried over $Na_2SO_4$, filtered, and concentrated. The residue was subjected to purification using reverse-phase HPLC to give 35 mg of pure product.

HPLC conditions: Gilson using Trilution software, with a phenomenex Luna 5u C18(2) 100A, AXIA. 50×30.00 mm 5 micron. 7.3-minute run (47 mL/min, 10% $ACN/H_2O$, 0.1% TFA to 40% $ACN/H_2O$, 0.1% TFA) with UV detection at 254 nm.

MS: $M(C_{22}H_{25}N_7O_3)$=435.49, $(M+1)^+$=436.2

$^1$HNMR (400 mHz, DMSO-$d_6$) δ ppm 7.00-7.90 (1H, m), 6.37 (1H, d, J=4.0 Hz), 3.41 (2H, m), 3.21 (2H, m), 2.35 (3H, s), 1.77 (2H, m).

Example 52

(4R)—N-[3-({4-[(3-methylphenyl)amino]-5-oxo-5,6-dihydropyrido[4,3-d]pyrimidin-2-yl}amino)propyl]-2-oxo-1,3-thiazolidine-4-carboxamide
(N4534-5)

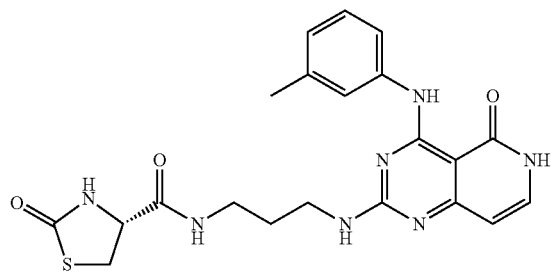 [SMILES: Cc1cccc(Nc2nc(NCCCNC(=O)[C@@H]3CSC(=O)N3)nc3cc[nH]c(=O)c23)c1]

The compound was prepared from 2-[(3-aminopropyl)amino]-4-[(3-methylphenyl)amino]pyrido[4,3-d]pyrimidin-5(6H)-one and (4R)—N-(3-aminopropyl)-2-oxo-1,3-thiazolidine-4-carboxamide using the procedure similar to that described for Example

MS: $M(C_{21}H_{23}N_7O_3S)$=453.52, $(M+1)^+$=454.0

$^1$HNMR (400 mHz, DMSO-$d_6$) δ ppm 8.29 (1H, m), 8.20 (1H, m), 7.76 (1H, m), 7.64 (1H, s), 7.57 (1H, m), 7.32 (1H, m), 7.05 (1H, m), 6.35 (1H, d, J=8.0 Hz), 2.45 (1H, m), 3.63 (1H, m), 3.44 (2H, m), 3.34 (1H, m), 3.20 (2H, m), 2.36 (3H, s), 1.77 (2H, m).

Intermediate 42

1,1-dimethylethyl methyl(2-{[3-({4-[(3-methylphenyl)amino]-5-oxo-5,6-dihydropyrido[4,3-d]pyrimidin-2-yl}amino)propyl]amino}-2-oxoethyl)carbamate

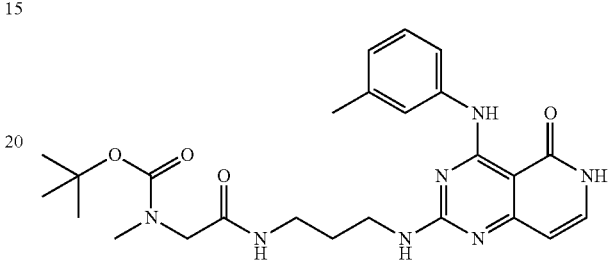

To a solution of 2-[(3-aminopropyl)amino]-4-[(3-methylphenyl)amino]pyrido[4,3-d]pyrimidin-5(6H)-one (50 mg, 0.114 mmol) in N,N-Dimethylformamide (DMF) (1.5 mL) were added N-{[(1,1-dimethylethyl)oxy]carbonyl}-N-methylglycine (25.9 mg, 0.137 mmol), 1H-1,2,3-benzotriazol-1-ol hydrate (34.9 mg, 0.228 mmol), 4-methylmorpholine (57.7 mg, 0.570 mmol), and N-[3-(dimethylamino)propyl]-N'-ethylcarbodiimide hydrochloride (28.4 mg, 0.148 mmol), and the reaction mixture was stirred for 2.5 h. It was then concentrated and the residue was subjected to reverse-phase HPLC purification to give 33 mg of the title compound.

MS; $M(C_{25}H_{33}N_7O_4)$=495.58, $(M+1)^+$=496.4

$^1$HNMR (400 mHz, DMSO-$d_6$) δ ppm 7.97 (1H, m), 7.76 (1H, m), 7.64 (1H, s), 7.56 (1H, m), 7.34 (1H, t, J=8.0 Hz), 7.04 (1H, d, J=4.0 Hz), 6.36 (1H, d, J=8.0 Hz), 3.73 (2H, m), 3.42 (2H, m), 3.17 (2H, m), 2.78 (3H, d J=8.0 Hz), 2.35 (3H, s), 1.74 (2H, m), 1.30-1.39 (9H, m).

Example 53

N[2]-methyl-N[1]-[3-({4-[(3-methylphenyl)amino]-5-oxo-5,6-dihydropyrido[4,3-d]pyrimidin-2-yl}amino)propyl]glycinamide

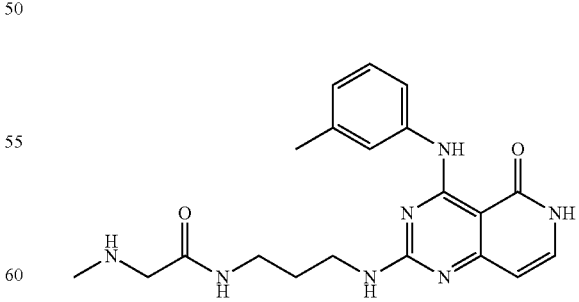

To a solution of 1,1-dimethylethyl methyl(2-{[3-({4[(3-methylphenyl)amino]-5-oxo-5,6-dihydropyrido[4,3-d]pyrimidin-2-yl}amino)propyl]amino}-2-oxoethyl)carbamate (30 mg, 0.061 mmol) in Dichloromethane (DCM) (1 mL) was added TFA (0.5 mL, 6.49 mmol), and the reaction mixture was stirred for 1.5 h. It was concentrated and the residue was further dried under high vacuum to give 30 mg of pure product.

MS: $M(C_{20}H_{25}N_7O_2)$=395.46, $(M+1)^+$=396.1

$^1$HNMR (400 mHz, DMSO-$d_6$) δ ppm 8.69 (2H, m), 8.49 (1H, m), 7.80 (1H, m), 7.65 (1H, s), 7.59 (1H, d, J=8.0 Hz), 7.35 (1H, t, J=8.0 Hz), 7.07 (1H, d, J=8.0 Hz), 6.37 (1H, d, J=4.0 Hz), 3.66 (2H, m), 3.47 (2H, m), 3.24 (2H, m), 2.54 (3H, m), 2.37 (3H, s), 1.79 (2H, m).

Example 54

N-[3-({4-[(3-methylphenyl)amino]-5-oxo-5,6-dihydropyrido[4,3-d]pyrimidin-2-yl}amino)propyl]-L-prolinamide

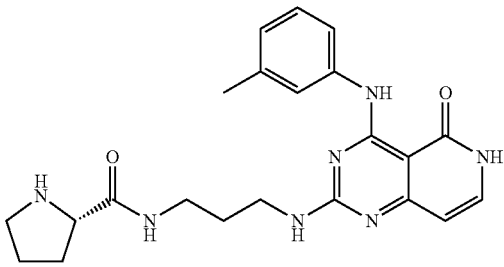 [SMILES: Cc1cccc(Nc2nc(NCCCNC(=O)[C@@H]3CCCN3)nc3cc[nH]c(=O)c23)c1]

The compound was prepared from 2-[(3-aminopropyl)amino]-4-[(3-methylphenyl)amino]pyrido[4,3-d]pyrimidin-5(6H)-one following the procedure similar to that described for Example 53.

MS: $M(C_{22}H_{27}N_7O_2)$=421.50, $(M+1)^+$=422.1

$^1$HNMR 4 mHz, DMSO-$d_6$) δ ppm 7.50-7.80 (4H, m), 7.34 (1H, t, J=8.0 Hz), 6.90-7.20 (2H, m), 6.32 (1H, d, J=6.0 Hz), 4.08 (2H, m), 3.45 (2H, m), 3.22 (4H, m), 2.36 (3H, s), 2.24 (1H, m), 1.82 (5H, m).

Biological Activity

PDK1 Enzymatic Assays
LEADseeker PDK1 Assay

Test compounds were dissolved to 1 mM in 100% DMSO and dispensed to appropriate columns of a 384-well plate. To generate dose-response curves, three-fold dilutions in 100% DMSO were performed across the plate to generate 11 concentrations for each test compound. Each plate can accommodate 32 test compounds for dose-response and 352 test compounds for single concentration determinations. Assay plates contained 0.1 uL of compound in appropriate wells of a 384-well plate. Two columns contained only 0.1 uL of 100% DMSO. These columns were used to determine the high and low control values. Prior to beginning the assay, 0.5M EDTA was added (1.5 uL/well for a 10 uL reaction volume) to the low control wells. Enzyme solution containing 25 mM MOPS, pH 7.5, 0.1 mg/mL BSA, 50 mM KCl, 0.5 mM CHAPS, 5 mM DTT, and 10 nM PDK1 was prepared immediately prior to addition of 5 uL to each well of the assay plate. Assay plates were incubated at room temperature for 30 minutes.

Substrate solution containing 25 mM MOPS, pH 7.5, 20 mM MgCl2, 50 mM KCl, 0.1 mg/mL BSA, 0.5 mM CHAPS, 5 mM DTT, 2 uM ATP (cold), 6 uCi/mL 33P-ATP, and 0.7 uM AKT1 biotinylated protein was prepared and left at room temperature, generally during the 30 min preincubation of enzyme with compound. Both solutions were mixed by gently inverting the tube prior to dispensing to the assay plate.

Substrate solution was added to the assay plate, 5 uL to each well, and the enzymatic reaction was allowed to progress at room temperature for 3 hours. The final concentration of reagents in the enzymatic reaction was 25 mM MOPS, pH 7.5, 10 mM MgCl2, 50 mM KCl, 0.1 mg/mL BSA, 0.5 mM CHAPS, 1 uM ATP (cold), 3 uCi/mL 33P-ATP, 5 mM DTT, 0.35 uM AKT1 biotinylated protein and 5 nM PDK1. The reaction was stopped by the addition of 10 uL of 5 mg/mL LEADseeker bead solution prepared by adding PBS and EDTA to 2 g dry beads to yield 400 mL of 50 mM EDTA in PBS.

Beads were allowed to settle in each well for at least 4-5 hours at room temperature, preferably overnight. The signal was stable for days after adding beads to plates. Plates were covered to limit exposure to light. The signal from each well was measured on a Viewlux™ ultraHTS microplate imager (PerkinElmer) using luminescence mode. DTT made fresh from solid is required. Fresh radioactive ATP yielded best signal to background.

PDK1 was generated from a baculovirus expression system and yielded human his-tagged full length protein purified to 80% using nickel and desalting columns (GRITS#24652). AKT1 was generated from a baculovirus expression system and yielded human protein (aa136-480) purified to 90% using nickel and Q Sepharose columns (GRITS#29020). The protein was biotinylated after purification.

Results:

Examples 1, 2, 12-13, 21, 25, 27, 30, 51-52, and 54 were not tested in the LeadSeeker PDK1 Assay. The remaining Examples were tested in the LeadSeeker PDK1 Assay and these Examples were found to be inhibitors of PDK1. The concentration of compound required to inhibit 50% ($IC_{50}$) of the PDK1 enzyme activity varied from 0.003 uM to 10 uM in the LeadSeeker PDK1 Assay.

Radiolabeled In Vitro Kinase Filter Binding Assay

PDK1 was pre-incubated (1 nM) for 1 hour at room temperature in 96-well low protein binding plates (Costar 3884) with a titration of compound in Kinase Assay Buffer (25 mM MOPS pH 7.5; 0.5 mM CHAPS; 10 mM MgCl2; 50 mM KCl; 1 mM DTT; 0.1 mg/ml BSA). Reactions were initiated by the addition of an 8× concentrated substrate pre-mix containing 2 uM Δ-PH AKT1 (aa136-480) and 5 uM ATP (containing 0.03 mCi/ml $γ^{33}P$ ATP). Following a 4 hour room temperature incubation, reactions were terminated by the addition of an equal volume 1% $H_3PO_4$. After a 10 minute incubation, the quenched reactions were transferred to phospho-cellulose filter plates (Millipore MAPH) pre-soaked with 0.5% $H_3PO_4$. The samples were filtered, washed with 0.5% $H_3PO_4$ and dried.

Plates were read on Microbeta scintillation counter (PerkinElmer) following addition of 50 μl/well Microscint 20.

PDK1-AKT Coupled In Vitro Kinase Assay.

The coupled assay measured the PDK1-dependent gain in activity of Δ-PH-AKT1 (aa136-480) in a continuous fluorescence intensity assay using sox-AKT peptide substrate (Invitrogen).

PDK1 (600 pM) was pre-incubated in a black 96-well half-area plate with a compound titration for 1 hour at room temperature in Kinase Assay Buffer. Reactions were initiated by the addition an equal volume of substrate premix containing 20 nM Δ-PH-AKT1, 10 uM ATP and 20 uM sox-peptide. Fluorescence was measured in an EnVision Multi Label Plate Reader (Perkin Elmer) using a Lance/Delfia mirror with the Fura2 380 excitation filter and the CFP 486 emission filter. A 6 hour endpoint from the progress curves was used to generate IC$_{50}$ curves across the inhibitor titration.

Cellular Assays:

Day 1

10,000 cells/well were plated in clear flat-bottomed 96-well plates (final volume was 105 ul) before noon. Last four wells in last column received media only. Plates were placed in 37° C. incubator overnight.

Compound plate was prepared in polypropylene round-bottomed 96-well plates; 8 compounds per plate, 11-point titrations of each (3-fold serial dilution), DMSO in last column (0.15% final concentration on cells). 15 ul of the stock compound was placed in first well, 10 ul DMSO in the rest; take 5 ul from first well was transferred and mixed in next, the dilution continued across plate (excluding last column); plate was sealed with foil lid and place at 4° C.

Day 2

Lysis buffer, inhibitors (4° C./–20° C.) and compound plates (4° C.) were thawed on bench top. 1× Tris wash buffer (WB) was made to fill reservoir on plate washer and top off bench supply, the centrifuge was turned on to allow it to cool.

MSD plates were blocked in blocking solution. 20 ml of 3% blocking solution were prepared for one plate (600 mg blocker A in 20 ml WB), 150 ul added per well and plates were incubated at ambient temperature for at least 1 hour. 300 ul of growth media (RPMI, 10% FBS) were added per well (682-fold dilution of compound) to each compound plate. 5 ul of compound dilution were added into each well (final volume 110 ul) on duplicate plates. Plates were place in 37° C. incubator for 30 min. For 10 ml of MSD Lysis buffer 200 ul protease inhibitor solution and 100 ul each of Phosphatase inhibitors I & II were added. Plates were removed post-incubation, media was aspirated with plate washer, plates were washed 1× with cold PBS, and add 80 ul of MSD Lysis buffer was added per well; plate were incubated on shaker at 4° C. for ≧30 min and spun in cold centrifuge at 2500 rpm for 10 min.

AKT Duplex Assay

Plates were washed 4 times with 200 ul/well Wash Buffer in plate washer. 60 ul of lysates were added per well, and plates were incubated on shaker at RT for 1 hour. During the incubation detection Ab was prepared (3 ml/plate; 2 ml Wash Buffer and 1 ml blocking solution with antibody at 10 nM). Wash step was repeated as above. 25 ul of antibody was added per well, and plates were incubate on shaker at ambient temperature for 1 hour. Wash step was repeated as above. 150 ul per well of 1× Read Buffer was added (dilute 4× stock in H$_2$O, 20 ml/plate), and plates were read immediately.

Cell Growth/Death Assay:

BT474, HCC1954, T-47D (human breast) and PC-3 (human prostate) cancer cells were cultured in RPMI-1640 containing 10% fetal bovine serum at 37° C. in 5% CO$_2$ incubator. Cells were split into T75 flask (Falcon #353136) two to three days prior to assay set up at density which yields approximately 70-80% confluence at time of harvest for assay. Cells were harvested using 0.25% trypsin-EDTA (Sigma #4049). Cell counts were performed on cell suspension using Trypan Blue exclusion staining. Cells were then plated in 384 well black flat bottom polystyrene (Greiner #781086) in 48 µl of culture media per well at 1,000 cells/well. All plates were placed at 5% CO$_2$, 37° C. overnight and test compounds were added the following day. One plate was treated with CellTiter-Glo (Promega #G7573) for a day 0 (t=0) measurement and read as described below. The test compounds were prepared in clear bottom polypropylene 384 well plates (Greiner#781280) with consecutive two fold dilutions. 4 µl of these dilutions were added to 105 µl culture media, after mixing the solution, 2 µl of these dilutions were added into each well of the cell plates. The final concentration of DMSO in all wells was 0.15%. Cells were incubated at 37° C., 5% CO$_2$ for 72 hours. Following 72 hours of incubation with compounds each plate was developed and read. CellTiter-Glo reagent was added to assay plates using a volume equivalent to the cell culture volume in the wells. Plates were shaken for approximately two minutes and incubated at room temperature for approximately 30 minutes and chemiluminescent signal was read on the Analyst GT (Molecular Devices) reader. Results were expressed as a percent of the t=0 and plotted against the compound concentration. Cell growth inhibition was determined for each compound by fitting the dose response with a 4 or 6 parameter curve fit using XLfit software and determining the concentration that inhibited 50% of the cell growth (gIC50) with the Y min as the t=0 and Y max as the DMSO control. Value from wells with no cells was subtracted from all samples for background correction.

What is claimed is:

1. A compound according to Formula I:

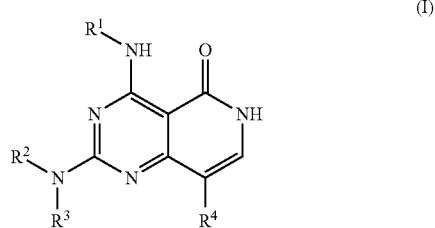

(I)

wherein:

R$^1$ is aryl, —CH$_2$-aryl, or heteroaryl each of which is optionally substituted with one to three R5;

R$^2$ is H, C$_1$-C$_6$ alkyl optionally substituted with one or two R$^6$, C$_3$-C$_6$ cycloalkyl optionally substituted with one to three R$^7$, or heterocycloalkyl optionally substituted with one to three R$^7$; and R3 is H, C$_1$-C$_6$ alkyl, or phenyl;

or

R$^2$ and R$^3$ are joined together with the nitrogen atom to which they are attached forming a saturated 4-7 membered heterocycloalkyl which may contain one additional N, S, or O atom and being optionally substituted with one to three C$_1$-C$_3$ alkyl groups optionally substituted with one OH, oxo, aryl, or —NR$^a$R$^b$;

R$^4$ is H, halo, C$_1$-C$_3$ alkyl, C$_1$-C$_3$ haloalkyl, cyano, C$_1$-C$_3$ alkoxy, NR$^a$R$^b$, aryl optionally substituted with one to three R$^5$, or heteroaryl optionally substituted with one to three R$^6$;

each R$^5$ is independently selected from the group consisting of halo, CN, C$_1$-C$_3$ alkoxy, heteroaryl, —S(O)$_2$R$^a$, —S(O)$_2$NR$^a$R$^b$, —NR$^a$S(O)$_2$R$^a$, —NR$^b$C(O)R$^a$, —C(O)NR$^a$R$^b$, —NR$^b$C(O)NR$^a$R$^b$, and C$_1$-C$_3$ alkyl optionally substituted by —NR$^a$R$^b$;

each R$^6$ is independently selected from the group consisting of OH, —NR$^a$R$^b$, —NR$^b$C(O)R$^a$, 1,1-cyclopropanedicarboxamide, heteroaryl, heterocycloalkyl, and aryl optionally substituted by S(O)$_2$NH$_2$;

each R$^7$ is independently selected from the group consisting of OH, C$_1$-C$_3$ alkoxy, —NR$^a$R$^b$, and C$_1$-C$_3$ alkyl optionally substituted by —NR$^a$R$^b$;

each R$^a$ is independently selected from the group consisting of H, heterocycloalkyl, and C$_1$-C$_3$ alkyl optionally substituted with one —NH$_2$ or NHCH$_3$; and each $R^b$ is independently H or $C_1$-$C_6$ alkyl; or a pharmaceutically acceptable salt thereof.

2. A compound according to claim 1 wherein $R^2$ is H, $C_1$-$C_6$ alkyl optionally substituted with one or two $R^6$, $C_3$-$C_6$ cycloalkyl optionally substituted with one to three $R^7$, or heterocycloalkyl optionally substituted with one to three $R^7$; and $R^3$ is H, $C_1$-$C_6$ alkyl, or phenyl; or a pharmaceutically acceptable salt thereof.

3. A compound according to claim 2 wherein $R^1$ is phenyl optionally substituted with one to three $R^5$; or a pharmaceutically acceptable salt thereof.

4. A compound according to claim 2 wherein $R^1$ is —$CH_2$-phenyl optionally substituted with one to three $R^5$; or a pharmaceutically acceptable salt thereof.

5. A compound according to claim 2 wherein $R^1$ is pyrazolyl or indazolyl optionally substituted with one to three $R^5$; or a pharmaceutically acceptable salt thereof.

6. A compound according to claim 2 wherein $R^2$ is $C_1$-$C_6$ alkyl optionally substituted with —$NR^aR^b$ and $R^3$ is H; or a pharmaceutically acceptable salt thereof.

7. A compound according to claim 2 wherein $R^2$ is pyrrolidinyl, piperidinyl, cyclohexyl, or cyclopropyl each of which is optionally substituted with one to three $R^7$; and $R^3$ is H, $C_1$-$C_6$ alkyl, or phenyl; or a pharmaceutically acceptable salt thereof.

8. A compound according to claim 6 wherein $R^4$ is H, methyl, or bromo; or a pharmaceutically acceptable salt thereof.

9. A pharmaceutical composition comprising a compound according to claim 1 or a pharmaceutically acceptable salt thereof in admixture with one or more pharmaceutically acceptable excipients.

* * * * *